| | | |
|---|---|---|
| (12) | United States Patent<br>Almblad | (10) Patent No.: US 11,382,994 B2<br>(45) Date of Patent: Jul. 12, 2022 |

(54) CLEAN IN PLACE ICE MAKING SYSTEM

(71) Applicant: Robert Almblad, Lynchburg, VA (US)

(72) Inventor: Robert Almblad, Lynchburg, VA (US)

( * ) Notice: Subject to any disclaimer, the term of this patent is extended or adjusted under 35 U.S.C. 154(b) by 457 days.

(21) Appl. No.: 15/848,193

(22) Filed: Dec. 20, 2017

(65) Prior Publication Data

US 2018/0207305 A1 Jul. 26, 2018

Related U.S. Application Data

(63) Continuation of application No. PCT/US2016/038929, filed on Jun. 23, 2016.

(60) Provisional application No. 62/281,362, filed on Jan. 21, 2016, provisional application No. 62/233,338, filed on Sep. 26, 2015, provisional application No. 62/196,109, filed on Jul. 23, 2015, provisional application No. 62/183,533, filed on Jun. 23, 2015.

(51) Int. Cl.
| | |
|---|---|
| *A61L 2/18* | (2006.01) |
| *A61L 2/20* | (2006.01) |
| *C01B 13/10* | (2006.01) |
| *F25C 5/182* | (2018.01) |
| *C01B 13/11* | (2006.01) |
| *F25C 5/185* | (2018.01) |

(52) U.S. Cl.
CPC ............... *A61L 2/183* (2013.01); *A61L 2/20* (2013.01); *C01B 13/10* (2013.01); *C01B 13/11* (2013.01); *F25C 5/182* (2013.01); *F25C 5/185* (2013.01); *A61L 2202/15* (2013.01); *F25C 2400/12* (2013.01)

(58) Field of Classification Search
CPC ........ A61L 2/183; A61L 2/20; A61L 2202/15; F25C 5/182; F25C 5/185; F25C 2400/12; C01B 13/10; C01B 13/11
See application file for complete search history.

(56) References Cited

U.S. PATENT DOCUMENTS

| | | |
|---|---|---|
| 3,068,660 A | 12/1962 | Council et al. |
| 6,132,629 A | 10/2000 | Boley |
| 6,167,711 B1 | 1/2001 | Slattery et al. |
| 6,287,515 B1 * | 9/2001 | Koosman ............... A61L 2/183<br>422/186.07 |
| 6,334,328 B1 | 1/2002 | Brill |

(Continued)

OTHER PUBLICATIONS

"Biotek Electrolytic Ozone Generation Technology," (www.biotek-ozone.com), Biotek Environmentel Science Ltd., 4 pages.

(Continued)

*Primary Examiner* — Sean E Conley
*Assistant Examiner* — Brendan A Hensel
(74) *Attorney, Agent, or Firm* — Michael J. Nickerson; Basch & Nickerson LLP

(57) ABSTRACT

An ice machine prevents micro-organism growth by utilizing a clean-in-place process. The ice making process of the ice making machine is turned OFF, and then ozonated water, from an ozonated water generation system, is pumped into a distribution system, within the ice making machine so that the ozonated water is sprayed onto surfaces of the ice making machine which are susceptible to micro-organism growth and/or scale. Exposing the surfaces to ozonated water kills the micro-organisms and rinses the dead micro-organisms out of the ice making machine.

2 Claims, 19 Drawing Sheets

(56) References Cited

U.S. PATENT DOCUMENTS

| | | | |
|---|---|---|---|
| 6,596,233 B2 * | 7/2003 | Berge | A61L 2/18 422/28 |
| 6,619,051 B1 | 9/2003 | Kilawee et al. | |
| 6,920,764 B2 | 7/2005 | Zevlakis | |
| 7,029,587 B2 | 4/2006 | Andrews | |
| 7,032,406 B2 | 4/2006 | Hollen et al. | |
| 7,059,140 B2 | 6/2006 | Zevlakis | |
| 7,469,548 B2 | 12/2008 | Brunner et al. | |
| 7,681,411 B2 | 3/2010 | DiLorenzo | |
| 8,661,837 B2 | 3/2014 | Kakita et al. | |
| 8,756,950 B2 | 6/2014 | Brunner et al. | |
| 9,017,485 B2 | 4/2015 | Murthy et al. | |
| 9,151,528 B2 | 10/2015 | Erbs et al. | |
| 2005/0218083 A1 | 10/2005 | Andrews | |
| 2007/0163283 A1 | 7/2007 | DiLorenzo | |
| 2007/0214809 A1 | 9/2007 | DiLorenzo | |
| 2008/0237368 A1 | 10/2008 | Hengsperger et al. | |
| 2009/0142225 A1 | 6/2009 | Tomqvist | |
| 2012/0031118 A1 | 2/2012 | Olson, Jr. et al. | |
| 2013/0039808 A1 | 7/2013 | Erbs et al. | |
| 2013/0174875 A1 | 7/2013 | Walker et al. | |
| 2016/0003515 A1 | 1/2016 | Brunner et al. | |
| 2016/0370061 A1 * | 12/2016 | Erbs | A61L 2/183 |
| 2019/0209719 A1 * | 7/2019 | Andersen | A61L 2/0088 |

OTHER PUBLICATIONS

"Anodic Materials for Electrocatalytic Ozone Generation," Hindawi Publishing Corporation, International Journal of Electrochemistry, vol. 2013, Article ID128248, 8 pages.

International Search Report for PCT/US2016/038929.

International Preliminary Report on Patentability for PCT/US2016/038929.

\* cited by examiner

CLEAN IN PLACE ICE MAKING SYSTEM

PRIORITY INFORMATION

The present application is a continuation application of PCT Patent Application Number PCT/US2016/038929 and claims priority, under 35 U.S.C. § 120, from PCT Patent Application Number PCT/US2016/038929, filed on Jun. 23, 2016. The entire content of PCT Patent Application Number PCT/US2016/038929, filed on Jun. 23, 2016, is hereby incorporated by reference.

PCT Patent Application Number PCT/US2016/038929, filed on Jun. 23, 2016, claims priority, under 35 U.S.C. § 119(e), from U.S. Provisional Patent Application Ser. No. 62/183,533, filed on Jun. 23, 2015. The entire content of U.S. Provisional Patent Application Ser. No. 62/183,533, filed on Jun. 23, 2015, is hereby incorporated by reference.

PCT Patent Application Number PCT/US2016/038929, filed on Jun. 23, 2016 claims priority, under 35 U.S.C. § 119(e), from U.S. Provisional Patent Application Ser. No. 62/196,109, filed on Jul. 23, 2015. The entire content of U.S. Provisional Patent Application Ser. No. 62/196,109, filed on Jul. 23, 2015, is hereby incorporated by reference.

PCT Patent Application Number PCT/US2016/038929, filed on Jun. 23, 2016 claims priority, under 35 U.S.C. § 119(e), from U.S. Provisional Patent Application Ser. No. 62/233,338, filed on Sep. 26, 2015. The entire content of U.S. Provisional Patent Application Ser. No. 62/233,338, filed on Sep. 26, 2015, is hereby incorporated by reference.

PCT Patent Application Number PCT/US2016/038929, filed on Jun. 23, 2016 claims priority, under 35 U.S.C. § 119(e), from U.S. Provisional Patent Application Ser. No. 62/281,362, filed on Jan. 21, 2016. The entire content of U.S. Provisional Patent Application Ser. No. 62/281,362, filed on Jan. 21, 2016, is hereby incorporated by reference.

BACKGROUND

Ice making systems and methods can expose the structural components and water/ice to the environment which may contain many contaminants. These contaminants need to be removed and/or cleaned from the ice making system. The following disclosure is directed to systems and methods that a clean-in-place system that kills harmful micro-organisms without having the ice machine being disassembled and washed.

U.S. Pat. No. 3,068,660 shows an ice making machine comprising a water tube in which ice is formed, a pump means for circulating water through the tube with a rate of flow sufficient to maintain substantially the entire volume of liquid water in the tube in circulation during the ice freezing operation, a means for refrigerating the water in the tube to form a deposit of ice in the tube, a means for sensing when a predetermined deposit of ice has formed in the tube, means actuated by the sensing means for initiating a thawing operation to loosen the deposited ice in the tube sufficiently to permit movement of the ice through the tube and a means responsive to initiation of the thawing operation for increasing the water flow rate to the tube to cause ejection of the ice from the tube. The entire content of U.S. Pat. No. 3,068,660 is hereby incorporated by reference.

U.S. Pat. No. 7,032,406 relates to an ice machine comprising a condensate collection unit disposed beneath an evaporator to collect condensate therefrom and a sump to remove condensate from the ice machine without making contact with recirculated water. The entire content of U.S. Pat. No. 7,032,406 is hereby incorporated by reference.

Published US Patent Application 2013/0174875-A1 discloses a system for automatically cleaning/sanitizing the water and ice making system on an ice machine, by eliminating the need to disassemble the unit in order to gain system access points to introduce cleaning and or sanitizing solutions and automating the sequence of events to insure proper cleaning. The entire content of Published US Patent Application 2013/0174875-A1 is hereby incorporated by reference.

Published US Patent Application 2013/0039808-A1 discloses a system for sanitizing ice storage equipment using an ozone generator to provide a sanitizing agent, which is circulated through an ice storage bin to cleanse interior surfaces of the ice storage bin and also surfaces of an ice dispenser. The entire content of Published US Patent Application 2013/0039808-A1 is hereby incorporated by reference.

U.S. Pat. No. 9,017,485 discloses an ice dispensing system that includes an ice hopper structure with a drain and a cleaning structure. The cleaning structure includes a pump linked to a spray mechanism positioned within the inner volume of the ice hopper structure to disperse a liquid on an inner surface of the ice hopper structure during a cleaning cycle of the ice dispensing mechanism. The entire content of U.S. Pat. No. 9,017,485 is hereby incorporated by reference.

In the various conventional systems for making and dispensing ice, the conventional ice maker have relied upon manual sanitizing, automatic sanitizing, ozone, chlorine dioxide, and/or ultraviolet light to reduce/prevent microbial growth.

With respect to manual cleaning, it is conventionally recommended by manufacturers to be done every six months. This process is time-consuming and may require hazardous chemicals.

Bin cleaning is difficult and disruptive and leads to possible ice waste. Also, bin cleaning is susceptible to timing and quality issues with respect to when or how well the manual process is performed.

With respect to conventional automatic sanitizing processes, these conventional processes only sanitize water contact areas, do not clean the bin or dispenser, and/or may lead to a false sense of security, making the operator incorrectly believe that the ice machine is being fully sanitized.

With respect to a conventional ozone sanitizing process, this conventional process is highly effective, but the process can be toxic if overdone or ineffective if done too little.

The conventional ozone process also does not provide a reliable measurement of the quality of the sanitizing process and reacts with rubber parts.

Lastly, ozone generators can be expensive and require periodic maintenance.

With respect to a conventional chlorine dioxide process, this conventional process is highly effective, but is costly and potentially hazardous.

With respect to a conventional ultraviolet light, this conventional process can be highly effective, but has significant safety and maintenance issues.

In summary, the various conventional systems have drawbacks, can rely on hazardous material, and/or do not all clean the ice bin, thereby preventing the realization of the production of clean ice.

As noted above, conventional ice machines make ice by recirculating water over and over an evaporator and making "clear" ice layer by layer generally in a cube or pillow shape. In the process of making the ice, the water freezes quickly and separates the minerals from the water in much the same way that boiling water or evaporating water separates minerals from the water.

The concentrated mineral sludge water is disposed, via an exterior drain, by using a sump pump.

The sump pump does necessarily not evacuate all the water from the reservoir, so there is a need to evacuate the last residue of this highly mineralized sludge water.

Even if all the sludge water is evacuated down the drain by spraying or washing the reservoir down with tap water, the tap water itself has dissolved minerals therein and when it dries, calcium or lime deposits called calcium magnesium or lime magnesium will remain, and the deposits will eventual build up into a hard "scale."

This scale will interfere with the operations of the ice machine by clogging valves, motors, and other functional parts. Also, this scale provides a perfect medium for microorganisms to establish themselves and grow into mold and/or slime.

Also, once scale forms on plastic and/or metal surfaces, scale is almost impossible to clean.

Since there is mineral build up and scale in ice machines, the ice machines need to be cleaned with descaling chemicals that are effective, but are poisonous if consumed.

Therefore, conventionally, the ice must be removed before cleaning scale from the ice machine, with the descaling chemicals.

However, since ice machines make ice very slowly, in order to make enough ice for daily ice usage in a typical restaurant, the ice machines need to make ice overnight to meet the demands for the next day.

Thus, emptying the ice machine for a descaling procedure can seriously interrupt or negatively impact a restaurant's business.

Consequently many or most of ice machine owners do not "de-scale" the ice machines when recommended by the manufacturer, resulting in costly and unnecessary repair work and downtime.

Moreover, conventional de-scaling can be harmful to the environment and/or water system.

Also, when the descaling chemicals are accidentally or mistakenly mixed with the sanitizing chemicals, the result can be the production of a poisonous gas.

Conventionally, descaling chemicals have been applied while using a cookie tray placed over the ice in an attempt to save the ice, resulting in customers consuming potentially contaminated ice.

In another conventional system, an ice machine runs the descaling and sanitizing solutions through the same water paths that are used to recirculate water to make ice. An example of such a system is illustrated in FIG. 1.

As illustrated in FIG. 1, an ice machine 20 includes a refrigerant circuit 22, a water circuit 50, a cleaning device 80, and an ice bin 76. Refrigerant circuit 22 includes a compressor 24, a pressure switch 25, a condenser 26, a drier 32, an expansion valve 36, and an evaporator 38 interconnected by piping 40 as shown. A motor 30 drives a fan 28 to provide cooling air to condenser 26.

Water circuit 50 includes a water reservoir 52, a water inlet 54, a control valve 56, a float switch 58, an overflow pipe 60, and a drain pan 64. A connection 71 connects a water supply 74 to water inlet 54 via a valve 73. Valve 73 is open during an ice making operation to provide water to water circuit 50 for making ice. Valve 73 is closed during cleaning operations.

A gas inlet 70 is connectable to a source 72 of pressurized gas such as air or carbon dioxide.

Cleaning device 80 is connectable via connection 92 and connection 71 to water inlet 54 to clean the water circuit components and evaporator 38 with a cleansing liquid 98. A valve 75 is disposed in connection 92 and is open during cleaning operations and closed during ice making operations.

Cleansing liquid 98 may include a cleaning, sanitizing, or a rinsing solution. For example, cleansing liquid 98 may contain a de-scaler, sanitizer, wash solution, clean water, or any other fluid used to remove contaminates. The cleansing liquid may also be a combination of any of these fluids.

Cleaning device 80 comprises a gas driven liquid or beverage pump 86 having a gas inlet 94, a liquid inlet 96, and a liquid outlet 93. An air pressure regulator 84 is connected via a connection 85 to gas input 94 of pump 86. Air regulator 84 is connected via connection 83 to a gas inlet 82 to receive pressurized gas from gas source 72.

Liquid inlet 96 is connected directly to a hose 90, which can be connected directly to or submerged into a container 95 that holds cleansing liquid 98, which is capable of cleaning, sanitizing, or rinsing. Liquid outlet 93 is connected via connection 92 and valve 75 to water inlet 54 of blended ice machine 20.

Connection 92 may be a hose with a quick connected or other connection directly to water inlet 54. Connections 71, 79, 83, 85, and 92 may be conduits made of a suitable material, e.g., metal, plastic, rubber, and the like.

A controller 100 controls refrigerant circuit 22 and water circuit 50 to make ice for storage in ice bin 76. Controller 100 also controls cleaning device 80 to provide a pressurized flow of cleansing liquid for in-place cleaning, sanitizing, and rinsing of water circuit 50, refrigerant circuit 22, and ice bin 76. A control panel 120 allows a user to interact with ice machine 20 to initiate the cleaning sequence.

Such a descaling/sanitizing utilizes two cycles: the "cleaning cycle" for calcium removal and the "sanitizing cycle" for killing and removing microorganisms. Each of these cycles replaces an ice making cycle.

In the cleaning cycle, instead of adding water for making ice, the system recirculates the water for a minute or two and then purges the water without making ice. The recirculation/purge process repeats itself a predetermined number of times, each time with fresh water. Thereafter, the sanitizing cycle performs a similar process.

More specifically, in a conventional system, for a cleaning cycle, a toxic calcium/lime cleaning solution/chemical may be added to the first of the predetermined number of recirculation/purge processes; wherein the remaining recirculation/purge processes attempt to flush out the cleaning solution and loosen/flush out calcium deposits by recirculating fresh water.

With respect to a conventional sanitizing cycle, chlorine may be added to the first of the predetermined number of recirculation/purge processes; wherein the remaining recirculation/purge processes attempt to flush out the sanitizing solution by recirculating fresh water.

Since the conventional cleaning cycles are done in the same water path as making ice, there is no provision for cleaning adjacent areas that have the high buildup of calcium due to splashing and/or water moving by capillary action through and/or upwards through the ring of calcium deposits or scale. The same phenomenon happens eventually with slime from microorganisms.

The calcium deposits or slime deposits provide a path for capillary action, thereby increasing slime and scale because the small amount of water moved by capillary action is evaporated between each cycle creating and adding more layers to the ring. These rings make it more possible to move more water by capillary action, eventually growing enough scale and slime to cause the ice machine to stop working. After such an incident, the ice machine needs to be disassembled and washed.

Therefore, it is desirable to provide an ice making system that includes a de-scaling system which avoids or reduces the problems of the conventional de-scaling processes.

It is further desirable to provide an ice making system that includes a clean-in-place system that kills harmful micro-organisms without having the ice machine being disassembled and washed.

It is also desirable to provide an ice making system that includes a clean-in-place system that kills harmful micro-organisms which utilizes a cleaning solution that is not noxious or harmful to a consumer.

It is additionally desirable to provide an ice making system that includes a clean-in-place system that kills harmful micro-organisms which utilizes a cleaning solution that is not noxious or harmful to a consumer and allows ice to remain in an ice storage bin during the cleaning process.

BRIEF DESCRIPTION OF THE DRAWING

The drawings are only for purposes of illustrating various embodiments and are not to be construed as limiting, wherein.

DETAILED DESCRIPTION OF THE DRAWINGS

Figure 1:
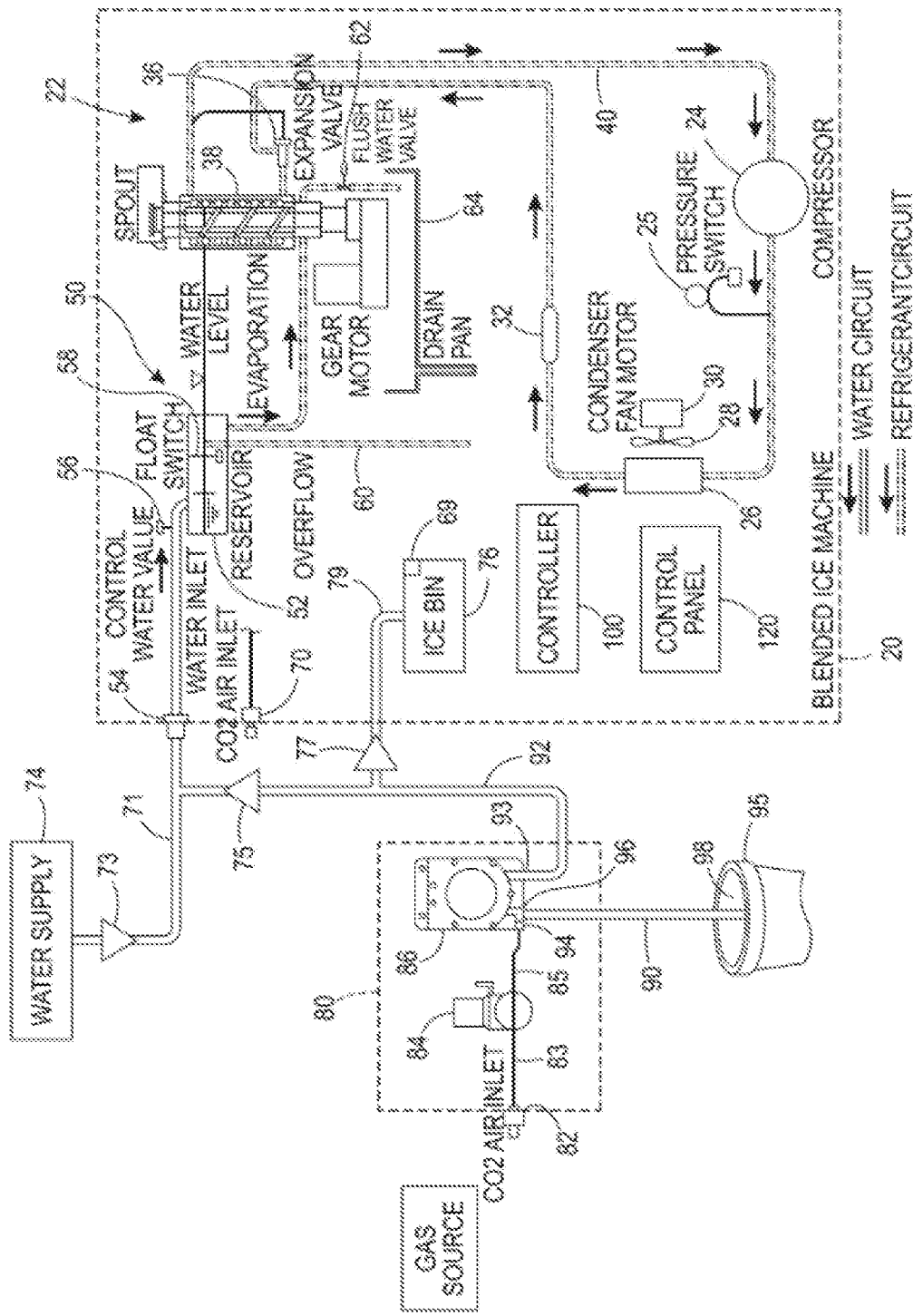
FIG. 1 illustrates a prior art system for cleaning an ice making machine.

For a general understanding, reference is made to the drawings. In the drawings, like references have been used throughout to designate identical or equivalent elements. It is also noted that the drawings may not have been drawn to scale and that certain regions may have been purposely drawn disproportionately so that the features and concepts could be properly illustrated.

Figure 2:
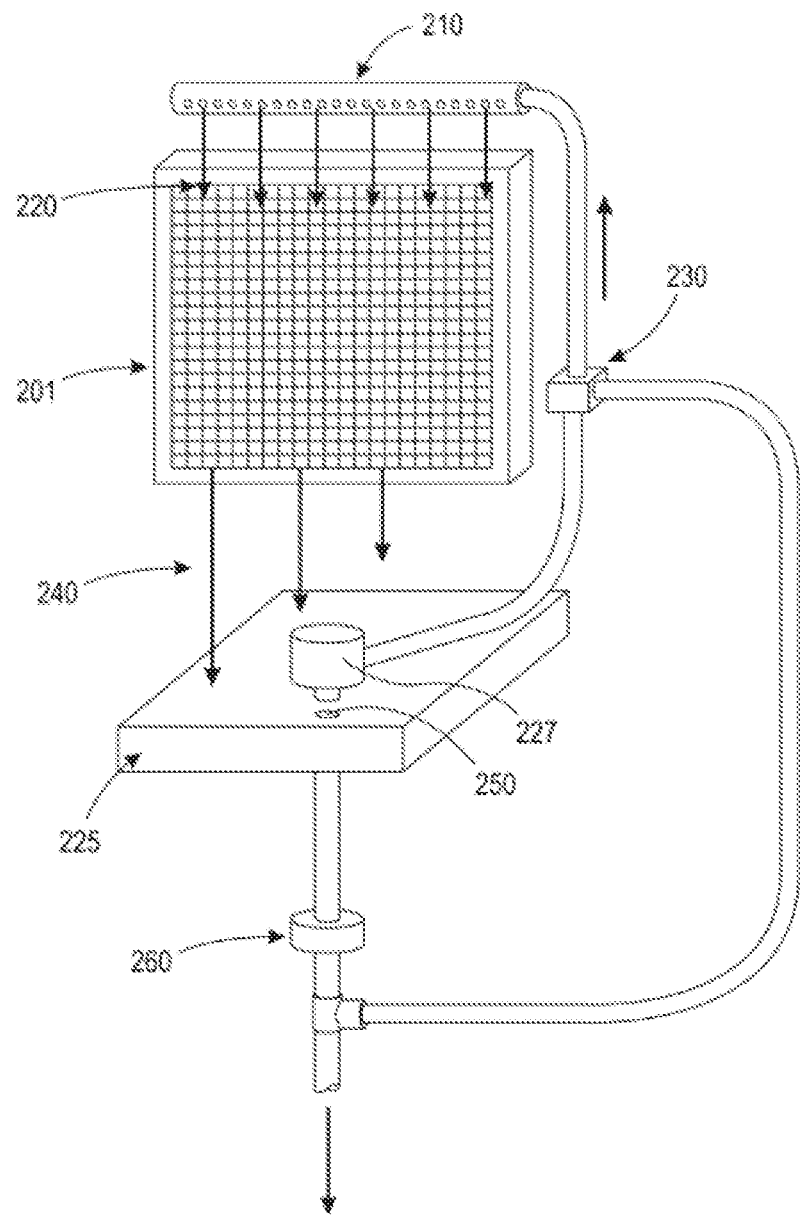
FIG. 2 illustrates an ice making system that removes mineralized water from a sump reservoir.

FIG. 2 illustrates an ice making system that removes mineralized water from a sump reservoir. As illustrated in FIG. 2, an ice making system includes an evaporator 201, over which water is distributed by a water distributor 210. The water distributor 210 receives water from a sump pump 227 that pumps water from a water reservoir or sump 225 to the water distributor 210. The water reservoir or sump 225 may be prefilled by a water source prior to the ice making process beginning or a water source may provide water directly to the water distributor 210 during the initial stages of the ice making process until the water level in the water reservoir or sump 225 reaches a predetermined level.

During the ice making process, the evaporator 201 become cold, from circulating refrigerant (not shown), such that the water 220, from the water distributor 210, freezes as the water interacts with the evaporator 201. Any water not freezing 240 falls to the water reservoir or sump 225 so that the unfrozen water 240 can be recirculated by the sump pump 227, via bypass valve 230, to the water distributor 210. The water 220 is recirculated to fall over the evaporator 201 until a predetermined amount of ice is formed.

After the ice making process is completed, the sump pump 227 is used to discharge the unused water 240 from the water reservoir or sump 225. The discharged water contains a high concentration of minerals because In the process of making the ice, the water freezes quickly and separates the minerals from the water in much the same way that boiling water or evaporating water separates minerals from the water.

Thus, after a batch of ice is made, there may be from 0.1 to 20 pounds of water with dissolved minerals left over in the water reservoir or sump 225.

However, using the sump pump 227 to discharge the water, via bypass valve 230, from the water reservoir or sump 225 does not necessarily remove all the mineralized water from the water reservoir or sump 225, thereby allowing an undesirable build-up of minerals in the water reservoir or sump 225 over time.

To remove this residual water and reduce the undesirable build-up of minerals in the water reservoir or sump 225 over time, the ice making machine of FIG. 2 includes a drain 250 and valve 260 to drain off the residual water. The drain 250 is located at the lowest point of the water reservoir or sump 225, usually under the sump pump 227.

The valve 260, connected to the drain 250, is opened after the sump pump 227 completes the discharge process to allow the residual water to exit the water reservoir or sump 225.

As illustrated in FIG. 2, the bypass valve 230 is utilized with the water recirculating system to direct the water from the sump pump 227 to either the water distributor 210, during an ice making process, or to an exterior drain, during the discharge process.

Various valves and tubing is used in the ice making system of FIG. 2. Moreover, the ice making system of FIG. 2 may include a controller (not shown) for controlling the operations of the various valves, the refrigerant system (not shown), and the sump pump 227.

Figure 3:
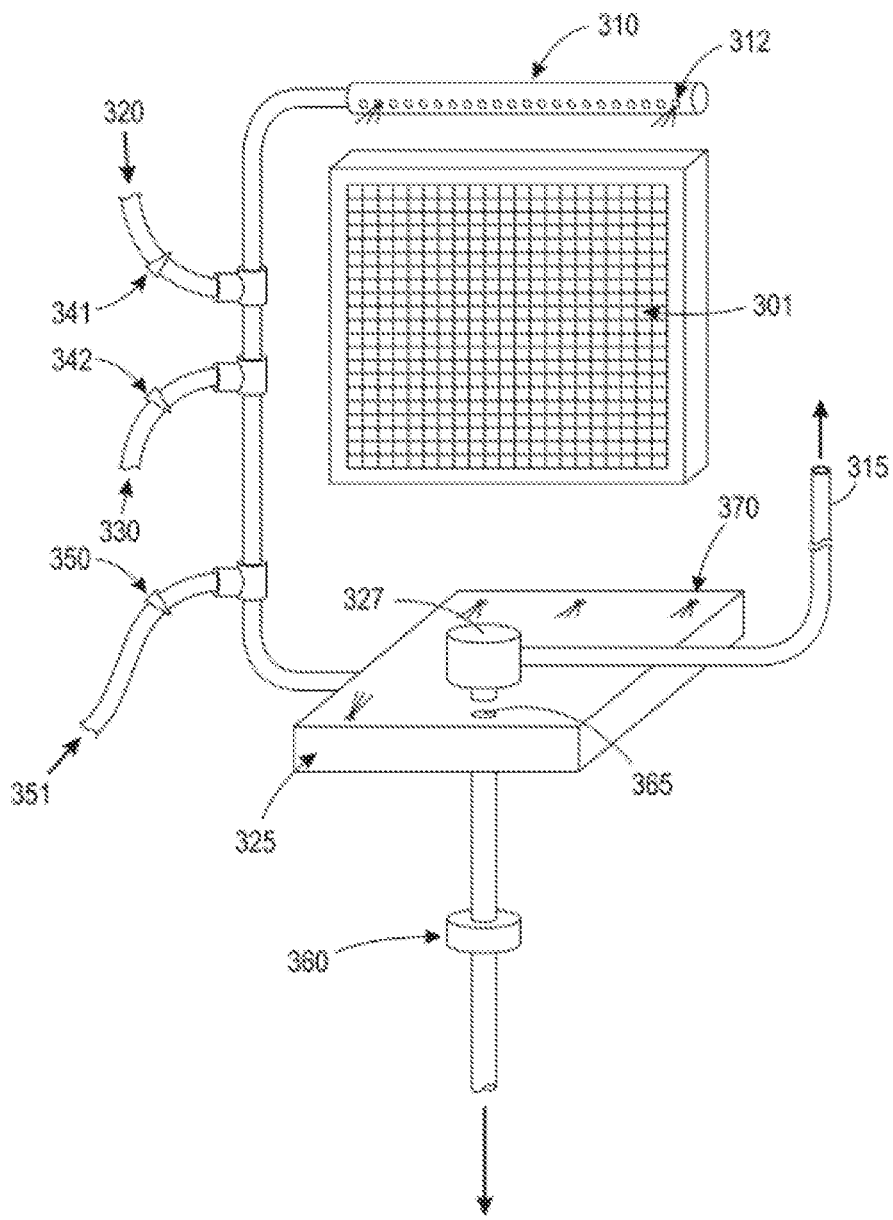
FIG. 3 illustrates an ice making system that includes a cleaning mechanism and a de-scaling mechanism.

FIG. 3 illustrates an ice making system that includes a cleaning mechanism and a de-scaling mechanism. As illustrated in FIG. 3, an ice making system includes an evaporator 301, over which water, via conduit 351 and valve 350, is distributed by a water distributor 310. The water distributor 310 receives water from a sump pump 327 that pumps water from a water reservoir or sump 325 to the water distributor 310.

During the ice making process, the evaporator 301 become cold, from circulating refrigerant (not shown), such that the water 312, from the water distributor 310, freezes as it interacts with the evaporator 301. Any water not freezing falls to the water reservoir or sump 325 so that it can be recirculated by the sump pump 327, via conduit 315, to the water distributor 310. The water is recirculated to fall over the evaporator 301 until a predetermined amount of ice is formed.

After the ice making process is completed, the sump pump 327 is used to discharge the used water, via conduit 315, a valve (not shown), and additional conduit (not shown), from the water reservoir or sump 325. The discharged water contains a high concentration of minerals because In the process of making the ice, the water freezes quickly and separates the minerals from the water in much the same way that boiling water or evaporating water separates minerals from the water.

Once the water is discharged, a cleaning process is initiated by introducing ozonated water (aqueous ozone), via conduit 320 and valve 341, into the ice making system. The introduced ozonated water is sprayed into the water distributor 310 to clean and sanitize the water distributor 310.

The ozonated water leaves the water distributor 310 and falls over the evaporator 301, thereby cleaning and sanitizing the evaporator 301 before falling into the water reservoir or sump 325.

It is noted that the ozonated water may be recirculated, by utilizing the sump pump 327, so that the ozonated water traverses the water distributor 310 and the evaporator 301 for a predetermined period of time. This recirculation of the ozonated water cleans and sanitizes the sump pump 327 and the tubing or conduit associated therewith.

The ozonated water may also be directly introduced, preferably sprayed 370, into the water reservoir or sump 325 to clean and sanitize the water reservoir or sump 325.

After the cleaning process, the ozonated water in the water reservoir or sump 325 is then discharged, via conduit 315, a valve (not shown), and additional conduit (not shown), by the sump pump 327.

However, using the sump pump 327 to discharge the water from the water reservoir or sump 325 does not necessarily remove all the ozonated water from the water reservoir or sump 325.

To remove this residual water, the ice making machine of FIG. 3 includes a drain 365 and valve 360 to drain off the residual water. The drain 365 is located at the lowest point of the water reservoir or sump 325, usually under the sump pump 327.

The valve 360, connected to the drain 365, is opened after the sump pump 327 completes the discharge process to allow the residual water to exit the water reservoir or sump 325.

A bypass valve, as illustrated in FIG. 2 (valve 230), may be utilized with the water recirculating system which directs the water from the sump pump 327 to either the water distributor 310, during the ice-making or cleaning process, or to an exterior drain, during the discharge process.

After the cleaning and discharge process is completed, the ice making system may be de-mineralized using de-mineralized water; such as, distilled water, filtered water, reverse-osmosis water, or soft water. The de-mineralized water is introduced, via conduit 330 and valve 342, preferably sprayed 312, into the water distributor 310 to de-scale the water distributor.

The de-mineralized water leaves the water distributor 310 and falls over the evaporator 301, thereby de-scaling the evaporator 301 before falling into the water reservoir or sump 325.

It is noted that the de-mineralized water may be recirculated, by utilizing the sump pump 327, so that the de-mineralized water traverses the water distributor 310 and the evaporator 301 for a predetermined period of time. This recirculation of the de-mineralized water de-scales the sump pump 327 and the tubing or conduit associated therewith.

The de-mineralized water may also be directed introduced, preferably sprayed 370, into the water reservoir or sump 325 to de-scale the water reservoir or sump.

After the de-scaling process, the water, containing minerals from the de-scaling process, in the water reservoir or sump 325 is then discharged, via conduit 315, a valve (not shown), and additional conduit (not shown), by the sump pump 327.

Various valves and tubing are used in the ice making system of FIG. 3. Moreover, the ice making system of FIG. 3 may include a controller for controlling the operations of the various valves, the refrigerant system (not shown), and the sump pump 327.

Figure 4:
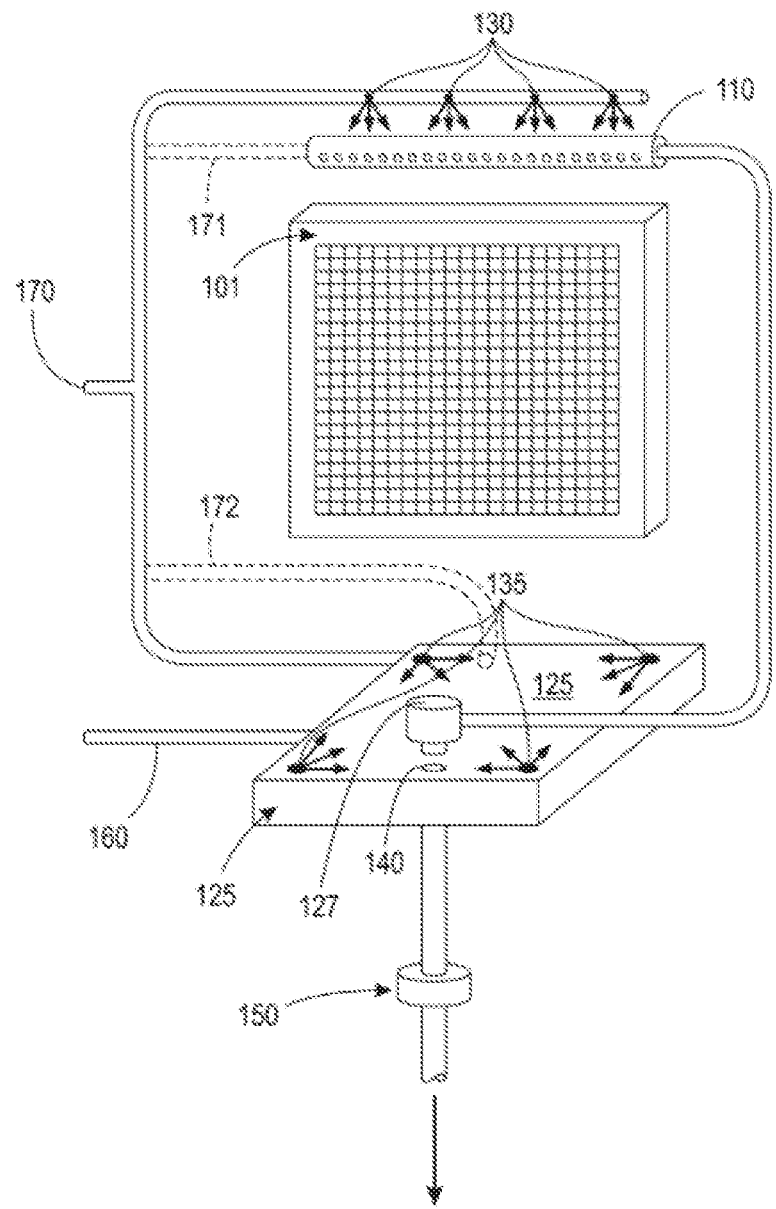
FIG. 4 illustrates an ice making system that includes a de-scaling mechanism.

FIG. 4 illustrates an ice making system that includes a de-scaling mechanism. As illustrated in FIG. 4, an ice making system includes an evaporator 101, over which water, from a water source 160, is distributed by a water distributor 110. The water distributor 110 receives water from a sump pump 120 that pumps, through tubing or conduits, water from a water reservoir or sump 125 to the water distributor 110.

During the ice making process, the evaporator 101 become cold, from circulating refrigerant (not shown), such that the water, from the water distributor 110, freezes as it interacts with the evaporator 101. Any water not freezing falls to the water reservoir or sump 125 so that it can be recirculated by the sump pump 127 to the water distributor 110. The water is recirculated to fall over the evaporator 101 until a predetermined amount of ice is formed.

After the ice making process is completed, the sump pump 127 is used to discharge the used water from the water reservoir or sump 125. The discharged water contains a high concentration of minerals because In the process of making the ice, the water freezes quickly and separates the minerals from the water in much the same way that boiling water or evaporating water separates minerals from the water.

Once the water is discharged, the ice making system is de-mineralized or de-scaled using de-mineralized water 170; such as, distilled water, filtered water, reverse-osmosis water, or soft water. The de-mineralized water is introduced, preferably sprayed by sprayers 130, into and around the water distributor 110 to de-scale the water distributor 110 and the area thereabout.

It is noted that de-mineralized water 171 may be introduced directly into the water distributor 110 without the use of sprayers 130.

It is further noted that the sprayers 130 associated with the water distributor 110, the area thereabout, and the evaporator 101 may be operated simultaneously with the introduction of the de-mineralized water 171 into the water distributor 110.

Also, the sprayers 130 associated with the water distributor 110, the area thereabout, and the evaporator 101 may be operated after or before the introduction of the de-mineralized water 171 into the water distributor 110.

It is noted that de-mineralized water 172 may be introduced directly into the water reservoir or sump 125 to be recirculated through the ice making system by the sump pump 127.

It is further noted that the sprayers 130 associated with the water distributor 110, the area therearound, and the evaporator 101 may be operated simultaneously with the recirculation of the de-mineralized water 172 through the water distributor 110.

Also, the sprayers 130 associated with the water distributor 110, the area therearound, and the evaporator 101 may be operated after or before the recirculation of the de-mineralized water 172 through the water distributor 110.

It is further noted that the sprayers 135 associated with the water reservoir or sump 125 may be operated simultaneously with the recirculation of the de-mineralized water 172 through the water distributor 110.

Also, the sprayers 135 associated with the water reservoir or sump 125 may be operated after or before the recirculation of the de-mineralized water 172 through the water distributor 110.

It is further noted that a de-scaling solution, such as a calcium/lime cleaning solution can be introduced into the ice making system using the same tubing or conduits and/or sprayers used by the de-mineralized water to de-scale the ice making system. If a cleaning solution is used, a fresh water flush is initiated thereafter to clean the cleaning solution from the surfaces of the ice making system. The flush operation would use the same tubing or conduits and/or sprayers used by the cleaning solution.

The de-mineralized water leaves the water distributor 110 and the area therearound and falls over the evaporator 101, thereby de-scaling the evaporator 101 before falling into the water reservoir or sump 125.

It is noted that the de-mineralized water may be recirculated, by utilizing the sump pump 120, so that the de-mineralized water traverses the water distributor 110 and evaporator 101 for a predetermined period of time. This recirculation of the de-mineralized water de-scales the sump pump 127 and the tubing or conduit associated therewith.

The de-mineralized water may also be directed introduced, preferably sprayed by sprayers 135, into the water reservoir or sump 125 to de-scale the water reservoir or sump 125.

After the de-scaling process, the water, containing minerals from the de-scaling process, in the water reservoir or sump 125 is then discharged by the sump pump 127.

However, using the sump pump 127 to discharge the water from the water reservoir or sump 125 does not necessarily remove all the water from the water reservoir or sump 125.

To remove this residual water, the ice making machine of FIG. 4 includes a drain 140 and valve 150 to drain off the residual water.

The drain 140 is located at the lowest point of the water reservoir or sump 125, usually under the sump pump 127.

The valve 150, connected to the drain 140, is opened after the sump pump 120 completes the discharge process to allow the residual water to exit the water reservoir or sump 125.

It is noted that during the draining process, the sprayers 135 can operate with de-mineralized water to assist the clearing of the residual scale from the water reservoir or sump 125 and into the drain 140.

A bypass valve may be utilized with the water recirculating system which directs the water from the sump pump 127 to either the water distributor 110, during the de-scaling process, or to an exterior drain, during the discharge process.

Various valves and tubing is used in the ice making system of FIG. 4. Moreover, the ice making system of FIG. 4 may include a controller for controlling the operations of the various valves, the refrigerant system (not shown), and the sump pump 127.

It is further noted that a sanitizing solution, such as ozonated water or a chlorine/water solution, can be introduced into the ice making system using the same tubing or conduits and/or sprayers used by the de-mineralized water to sanitize the ice making system.

Upon completion of the sanitizing process, the sanitizing solution is discharged from the water reservoir or sump 125 using the sump pump 127. However, using the sump pump 127 to discharge the sanitizing solution from the water reservoir or sump 125 does not necessarily remove all the sanitizing solution from the water reservoir or sump 125.

To remove this residual sanitizing solution, the valve 150, connected to the drain 140, is opened after the sump pump 127 completes the discharge process to allow the residual sanitizing solution to exit the water reservoir or sump 125.

It is noted that during the draining process, the sprayers 135 can operate with de-mineralized water to assist the clearing of the residual sanitizing solution from the water reservoir or sump 125 and into the drain 140.

Figure 5:
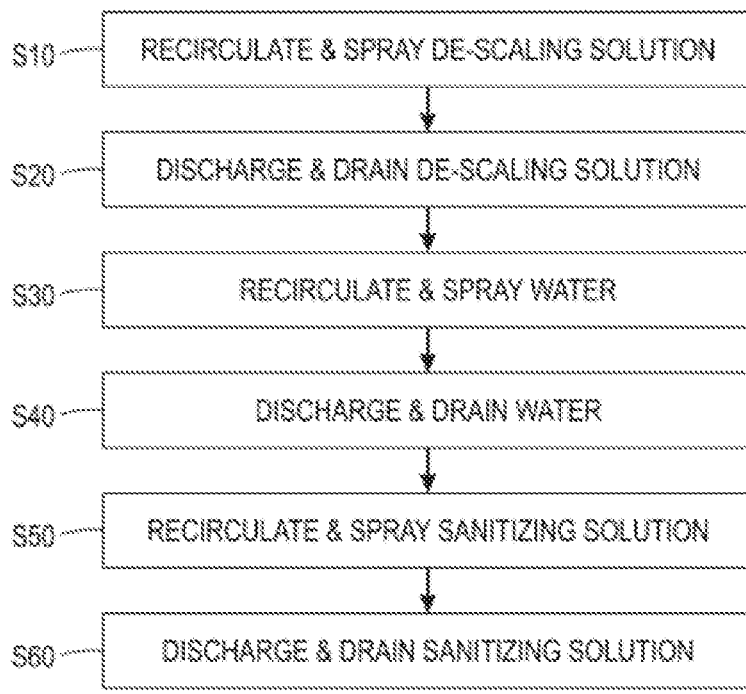
FIGS. 5 through 8 illustrate flowcharts showing various de-scaling and sanitizing processes.

FIG. 5 illustrates a de-scaling/sanitizing process. As illustrated in FIG. 5, at step S10, a de-scaling solution, such as a calcium/lime cleaning solution is introduced into the ice making system. It is noted that de-scaling solution may be introduced directly into the water distributor without the use of sprayers, introduced directly into the water reservoir or sump to be recirculated through the ice making system by the sump pump, or introduced by sprayers associated with the water distributor, the area therearound, and the evaporator.

It is further noted that the sprayers associated with the water distributor, the area therearound, and the evaporator may be operated simultaneously with the introduction of the de-scaling solution into the water distributor.

Also, the sprayers associated with the water distributor, the area therearound, and the evaporator may be operated after or before the introduction of the de-scaling solution into the water distributor.

It is further noted that the sprayers associated with the water distributor, the area therearound, and the evaporator may be operated simultaneously with the recirculation of the de-scaling solution through the water distributor.

Also, the sprayers associated with the water distributor, the area therearound, and the evaporator may be operated after or before the recirculation of the de-scaling solution through the water distributor.

It is further noted that sprayers associated with the water reservoir or sump may be operated simultaneously with the recirculation of the de-scaling solution through the water distributor.

Also, the sprayers associated with the water reservoir or sump may be operated after or before the recirculation of the de-scaling solution through the water distributor.

At step S20, the de-scaling solution is discharged, by the sump pump, from the water reservoir or sump, and thereafter, a drain is opened to drain the residual de-scaling solution.

At step S30, water is introduced into the ice making system to remove any residual de-scaling solution on the surfaces of the ice making machine. Step S30 may be repeated a predetermined number of times to insure a proper removal of the de-scaling solution.

It is noted that the water may be introduced directly into the water distributor without the use of sprayers, introduced directly into the water reservoir or sump to be recirculated through the ice making system by the sump pump, or introduced by sprayers associated with the water distributor, the area therearound, and the evaporator.

It is further noted that the sprayers associated with the water distributor, the area therearound, and the evaporator may be operated simultaneously with the introduction of the water into the water distributor.

Also, the sprayers associated with the water distributor, the area therearound, and the evaporator may be operated after or before the introduction of the water into the water distributor.

It is further noted that the sprayers associated with the water distributor, the area therearound, and the evaporator may be operated simultaneously with the recirculation of the water through the water distributor.

Also, the sprayers associated with the water distributor, the area therearound, and the evaporator may be operated after or before the recirculation of the water through the water distributor.

It is further noted that sprayers associated with the water reservoir or sump may be operated simultaneously with the recirculation of the water through the water distributor.

Also, the sprayers associated with the water reservoir or sump may be operated after or before the recirculation of the water through the water distributor.

At step S40, the water is discharged, by the sump pump, from the water reservoir or sump, and thereafter, a drain is opened to drain the residual water.

At step S50, a sanitizing solution, such as ozonated water or chlorinated water is introduced into the ice making system to kill and remove any microorganisms on the surfaces of the ice making machine. Step S50 may be repeated a predetermined number of times to insure a proper killing and removal of the microorganisms.

It is noted that the sanitizing solution may be introduced directly into the water distributor without the use of sprayers, introduced directly into the water reservoir or sump to be recirculated through the ice making system by the sump pump, or introduced by sprayers associated with the water distributor, the area therearound, and the evaporator.

It is further noted that the sprayers associated with the water distributor, the area therearound, and the evaporator may be operated simultaneously with the introduction of the sanitizing solution into the water distributor.

Also, the sprayers associated with the water distributor, the area therearound, and the evaporator may be operated after or before the introduction of the sanitizing solution into the water distributor.

It is further noted that the sprayers associated with the water distributor, the area therearound, and the evaporator may be operated simultaneously with the recirculation of the sanitizing solution through the water distributor.

Also, the sprayers associated with the water distributor, the area therearound, and the evaporator may be operated after or before the recirculation of the sanitizing solution through the water distributor.

It is further noted that sprayers associated with the water reservoir or sump may be operated simultaneously with the recirculation of the sanitizing solution through the water distributor.

Also, the sprayers associated with the water reservoir or sump may be operated after or before the recirculation of the sanitizing solution through the water distributor.

At step S60, the sanitizing solution is discharged, by the sump pump, from the water reservoir or sump, and thereafter, a drain is opened to drain the residual sanitizing solution.

Figure 6:
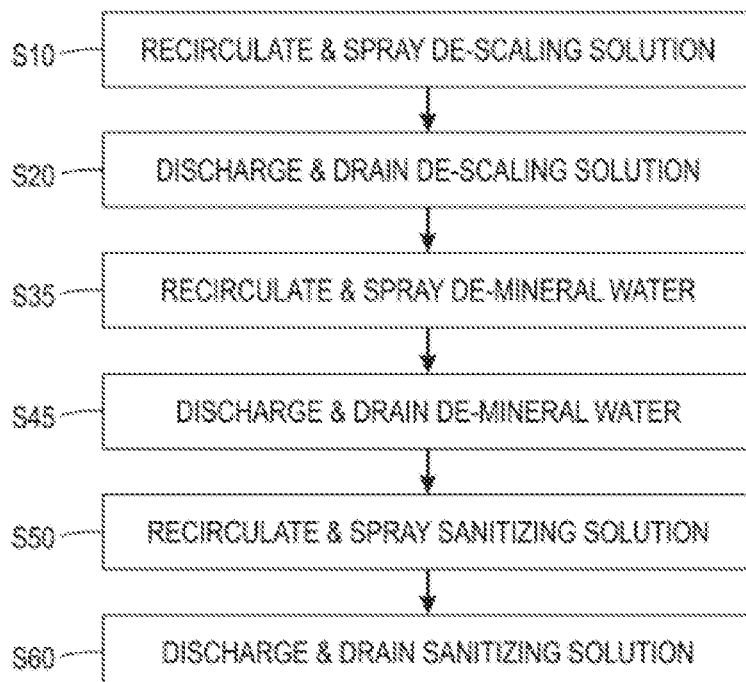

FIG. 6 illustrates a de-scaling/sanitizing process. As illustrated in FIG. 6, at step S10, a de-scaling solution, such as a calcium/lime cleaning solution is introduced into the ice making system. It is noted that de-scaling solution may be introduced directly into the water distributor without the use of sprayers, introduced directly into the water reservoir or sump to be recirculated through the ice making system by the sump pump, or introduced by sprayers associated with the water distributor, the area therearound, and the evaporator.

It is further noted that the sprayers associated with the water distributor, the area therearound, and the evaporator may be operated simultaneously with the introduction of the de-scaling solution into the water distributor.

Also, the sprayers associated with the water distributor, the area therearound, and the evaporator may be operated after or before the introduction of the de-scaling solution into the water distributor.

It is further noted that the sprayers associated with the water distributor, the area therearound, and the evaporator may be operated simultaneously with the recirculation of the de-scaling solution through the water distributor.

Also, the sprayers associated with the water distributor, the area therearound, and the evaporator may be operated after or before the recirculation of the de-scaling solution through the water distributor.

It is further noted that sprayers associated with the water reservoir or sump may be operated simultaneously with the recirculation of the de-scaling solution through the water distributor.

Also, the sprayers associated with the water reservoir or sump may be operated after or before the recirculation of the de-scaling solution through the water distributor.

At step S20, the de-scaling solution is discharged, by the sump pump, from the water reservoir or sump, and thereafter, a drain is opened to drain the residual de-scaling solution.

At step S35, de-mineralized water, such as distilled water, filtered water, reverse osmosis water, or soft water, is introduced into the ice making system to remove any residual de-scaling solution on the surfaces of the ice making machine. Step S35 may be repeated a predetermined number of times to insure a proper removal of the de-scaling solution.

It is noted that the de-mineralized water may be introduced directly into the water distributor without the use of sprayers, introduced directly into the water reservoir or sump to be recirculated through the ice making system by the sump pump, or introduced by sprayers associated with the water distributor, the area therearound, and the evaporator.

It is further noted that the sprayers associated with the water distributor, the area therearound, and the evaporator may be operated simultaneously with the introduction of the de-mineralized water into the water distributor.

Also, the sprayers associated with the water distributor, the area therearound, and the evaporator may be operated after or before the introduction of the de-mineralized water into the water distributor.

It is further noted that the sprayers associated with the water distributor, the area therearound, and the evaporator may be operated simultaneously with the recirculation of the de-mineralized water through the water distributor.

Also, the sprayers associated with the water distributor, the area therearound, and the evaporator may be operated after or before the recirculation of the de-mineralized water through the water distributor.

It is further noted that sprayers associated with the water reservoir or sump may be operated simultaneously with the recirculation of the de-mineralized water through the water distributor.

Also, the sprayers associated with the water reservoir or sump may be operated after or before the recirculation of the de-mineralized water through the water distributor.

At step S45, the de-mineralized water is discharged, by the sump pump, from the water reservoir or sump, and thereafter, a drain is opened to drain the residual de-mineralized water.

At step S50, a sanitizing solution, such as ozonated water or chlorinated water is introduced into the ice making system to kill and remove any microorganisms on the surfaces of the ice making machine. Step S50 may be repeated a predetermined number of times to insure a proper killing and removal of the microorganisms.

It is noted that the sanitizing solution may be introduced directly into the water distributor without the use of sprayers, introduced directly into the water reservoir or sump to be recirculated through the ice making system by the sump pump, or introduced by sprayers associated with the water distributor, the area therearound, and the evaporator.

It is further noted that the sprayers associated with the water distributor, the area therearound, and the evaporator may be operated simultaneously with the introduction of the sanitizing solution into the water distributor.

Also, the sprayers associated with the water distributor, the area therearound, and the evaporator may be operated after or before the introduction of the sanitizing solution into the water distributor.

It is further noted that the sprayers associated with the water distributor, the area therearound, and the evaporator may be operated simultaneously with the recirculation of the sanitizing solution through the water distributor.

Also, the sprayers associated with the water distributor, the area therearound, and the evaporator may be operated after or before the recirculation of the sanitizing solution through the water distributor.

It is further noted that sprayers associated with the water reservoir or sump may be operated simultaneously with the recirculation of the sanitizing solution through the water distributor.

Also, the sprayers associated with the water reservoir or sump may be operated after or before the recirculation of the sanitizing solution through the water distributor.

At step S60, the sanitizing solution is discharged, by the sump pump, from the water reservoir or sump, and thereafter, a drain is opened to drain the residual sanitizing solution.

Figure 7:
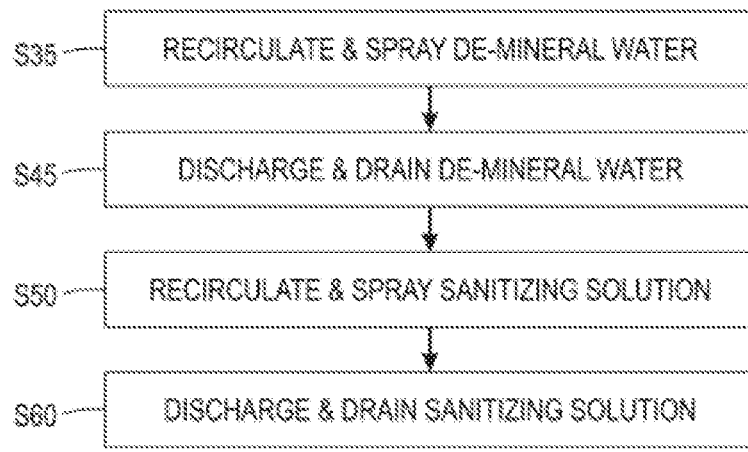

FIG. 7 illustrates a de-scaling/sanitizing process. As illustrated in FIG. 7, at step S35, de-mineralized water, such as distilled water, filtered water, reverse osmosis water, or soft water, is introduced into the ice making system to remove any residual de-scaling solution on the surfaces of the ice making machine. Step S35 may be repeated a predetermined number of times to insure a proper removal of the de-scaling solution.

It is noted that the de-mineralized water may be introduced directly into the water distributor without the use of sprayers, introduced directly into the water reservoir or sump to be recirculated through the ice making system by the sump pump, or introduced by sprayers associated with the water distributor, the area therearound, and the evaporator.

It is further noted that the sprayers associated with the water distributor, the area therearound, and the evaporator may be operated simultaneously with the introduction of the de-mineralized water into the water distributor.

Also, the sprayers associated with the water distributor, the area therearound, and the evaporator may be operated after or before the introduction of the de-mineralized water into the water distributor.

It is further noted that the sprayers associated with the water distributor, the area therearound, and the evaporator may be operated simultaneously with the recirculation of the de-mineralized water through the water distributor.

Also, the sprayers associated with the water distributor, the area therearound, and the evaporator may be operated after or before the recirculation of the de-mineralized water through the water distributor.

It is further noted that sprayers associated with the water reservoir or sump may be operated simultaneously with the recirculation of the de-mineralized water through the water distributor.

Also, the sprayers associated with the water reservoir or sump may be operated after or before the recirculation of the de-mineralized water through the water distributor.

At step S45, the de-mineralized water is discharged, by the sump pump, from the water reservoir or sump, and thereafter, a drain is opened to drain the residual de-mineralized water.

At step S50, a sanitizing solution, such as ozonated water or chlorinated water is introduced into the ice making system to kill and remove any microorganisms on the surfaces of the ice making machine. Step S50 may be repeated a predetermined number of times to insure a proper killing and removal of the microorganisms.

It is noted that the sanitizing solution may be introduced directly into the water distributor without the use of sprayers, introduced directly into the water reservoir or sump to be recirculated through the ice making system by the sump pump, or introduced by sprayers associated with the water distributor, the area therearound, and the evaporator.

It is further noted that the sprayers associated with the water distributor, the area therearound, and the evaporator may be operated simultaneously with the introduction of the sanitizing solution into the water distributor.

Also, the sprayers associated with the water distributor, the area therearound, and the evaporator may be operated after or before the introduction of the sanitizing solution into the water distributor.

It is further noted that the sprayers associated with the water distributor, the area therearound, and the evaporator may be operated simultaneously with the recirculation of the sanitizing solution through the water distributor.

Also, the sprayers associated with the water distributor, the area therearound, and the evaporator may be operated after or before the recirculation of the sanitizing solution through the water distributor.

It is further noted that sprayers associated with the water reservoir or sump may be operated simultaneously with the recirculation of the sanitizing solution through the water distributor.

Also, the sprayers associated with the water reservoir or sump may be operated after or before the recirculation of the sanitizing solution through the water distributor.

At step S60, the sanitizing solution is discharged, by the sump pump, from the water reservoir or sump, and thereafter, a drain is opened to drain the residual sanitizing solution.

Figure 8:
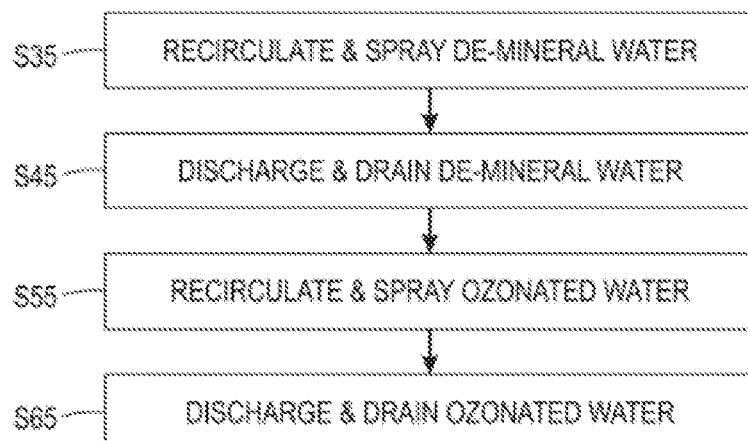

FIG. 8 illustrates a de-scaling/sanitizing process. As illustrated in FIG. 8, at step S35, de-mineralized water, such as distilled water, filtered water, reverse osmosis water, or soft water, is introduced into the ice making system to remove any residual de-scaling solution on the surfaces of the ice making machine. Step S35 may be repeated a predetermined number of times to insure a proper removal of the de-scaling solution.

It is noted that the de-mineralized water may be introduced directly into the water distributor without the use of sprayers, introduced directly into the water reservoir or sump to be recirculated through the ice making system by the sump pump, or introduced by sprayers associated with the water distributor, the area therearound, and the evaporator.

It is further noted that the sprayers associated with the water distributor, the area therearound, and the evaporator may be operated simultaneously with the introduction of the de-mineralized water into the water distributor.

Also, the sprayers associated with the water distributor, the area therearound, and the evaporator may be operated after or before the introduction of the de-mineralized water into the water distributor.

It is further noted that the sprayers associated with the water distributor, the area therearound, and the evaporator may be operated simultaneously with the recirculation of the de-mineralized water through the water distributor.

Also, the sprayers associated with the water distributor, the area therearound, and the evaporator may be operated after or before the recirculation of the de-mineralized water through the water distributor.

It is further noted that sprayers associated with the water reservoir or sump may be operated simultaneously with the recirculation of the de-mineralized water through the water distributor.

Also, the sprayers associated with the water reservoir or sump may be operated after or before the recirculation of the de-mineralized water through the water distributor.

At step S45, the de-mineralized water is discharged, by the sump pump, from the water reservoir or sump, and thereafter, a drain is opened to drain the residual de-mineralized water.

At step S50, ozonated water is introduced into the ice making system to kill and remove any microorganisms on the surfaces of the ice making machine. Step S50 may be repeated a predetermined number of times to insure a proper killing and removal of the microorganisms.

It is noted that the ozonated water may be introduced directly into the water distributor without the use of sprayers, introduced directly into the water reservoir or sump to be recirculated through the ice making system by the sump pump, or introduced by sprayers associated with the water distributor, the area therearound, and the evaporator.

It is further noted that the sprayers associated with the water distributor, the area therearound, and the evaporator may be operated simultaneously with the introduction of the ozonated water into the water distributor.

Also, the sprayers associated with the water distributor, the area therearound, and the evaporator may be operated after or before the introduction of the ozonated water into the water distributor.

It is further noted that the sprayers associated with the water distributor, the area therearound, and the evaporator may be operated simultaneously with the recirculation of the ozonated water through the water distributor.

Also, the sprayers associated with the water distributor, the area therearound, and the evaporator may be operated after or before the recirculation of the ozonated water through the water distributor.

It is further noted that sprayers associated with the water reservoir or sump may be operated simultaneously with the recirculation of the ozonated water through the water distributor.

Also, the sprayers associated with the water reservoir or sump may be operated after or before the recirculation of the ozonated water through the water distributor.

At step S60, the ozonated water is discharged, by the sump pump, from the water reservoir or sump, and thereafter, a drain is opened to drain the residual ozonated water.

In summary, the above described sprayers cover all the critical surfaces of the ice making machine, including the joints and the internal top side of the horizontal water distributor tubes, which conventionally are only half full of water.

The ozonated water, via the sprayers, also cleans all these critical surfaces.

It is also noted that the use of de-mineralized water for de-scaling eliminates the need to use potentially poisonous de-scaling solutions.

It is further note that a small vibration source can be attached to the water distributor, the evaporator, and/or the water reservoir/sump to add a vibrational noise to the surfaces of these devices to assist in breaking up the scale and facilitate an effective removal thereof.

In the water reservoir or sump, which collects the recirculated water during the ice making process, a drain is placed at the lowest point, which is normally just under the sump pump. This drain has a valve that remains closed during the ice making process, but when the batch of ice is finished, the drain is opened and the concentrated water/mineral sludge solution is allowed to exit by gravity, for example.

Once the sludge exits, sprayers or nozzles are activated with tap water to wash or drive the sediment down the drain. Once this is done, the drain valve is closed and tap water partially fills the water tray or reservoir and then the sump pump is turned on to pump the water down a bypass dump valve of the recirculating circuit.

This process cleans the tray, the pump, the drain valve, and the bypass valve with tap water by washing the majority of the harmful scale causing minerals down the drain.

However, due to surface tension, droplets of tap water may remain on all these surfaces, which, in turn may cause the build-up of scale as the water evaporates.

To prevent the build-up, sprayers spray a mineral free water source (like distilled water, filtered water, reverse osmosis water or a soft water), using the same process of spraying, as described above with respect to tap water, the water reservoir or sump, the drain valve, the pump, and the bypass valve. This leaves the various parts clean of minerals so that when the mineral free water dries, it does not leave a mineral deposit.

At the top of the ice machine, where the recirculating water is distributed across the evaporator to make ice, sprayers or nozzles are used in a similar manner as cleaning the water reservoir or sump.

First, tap water is used to clean mineral laden water off of all surfaces that come into contact with this "sludgy" water. This washes the concentrated minerals down to the water tray where the mineral laden water is disposed of down the drain. Then the sprayers/nozzles are switched to a mineral free source of water and all these parts are washed down again.

It is noted that the sprayers can also be used with a cleaning solution to provide a clean-in-place ice making machine. In the cleaning configuration, the sprayers spray ozonated water for sanitizing and cleaning, which further reduces the chemicals in the environment.

It is further noted that spraying ozonated water at the side walls of an ice bin to sanitize and clean an ice in can allow for the cleaning of the ice bin without requiring the ice to be removed.

In addition, the above described de-scaling/sanitizing processes and systems involve wetting all food contact surface areas, all joints and seals with de-mineralized water and a sanitizer, preferably ozonated water. The above described de-scaling/sanitizing processes provide a more effective cleaning and sanitizing solution to avoid the need to disassemble and washed to clean the ice making machine.

The above described de-scaling/sanitizing processes and systems uses certain techniques to not only clean and sanitize the same water path for making ice, but also clean and sanitize all the splash areas, areas of high moisture, areas wetted by water surface tension migration (dripping), and areas wetted by capillary action, etc.

The above described de-scaling/sanitizing processes and systems can be utilized to clean and sanitize the ice bin and walls, which can be done automatically, without removing the ice.

The above described de-scaling/sanitizing processes and systems involve evacuating and rinsing all the water surfaces first with tap water or a de-scaling solution followed by a "spot free rinse" so that no water with minerals is allowed to dry on any surface in or near the water path for making ice.

Figure 9:
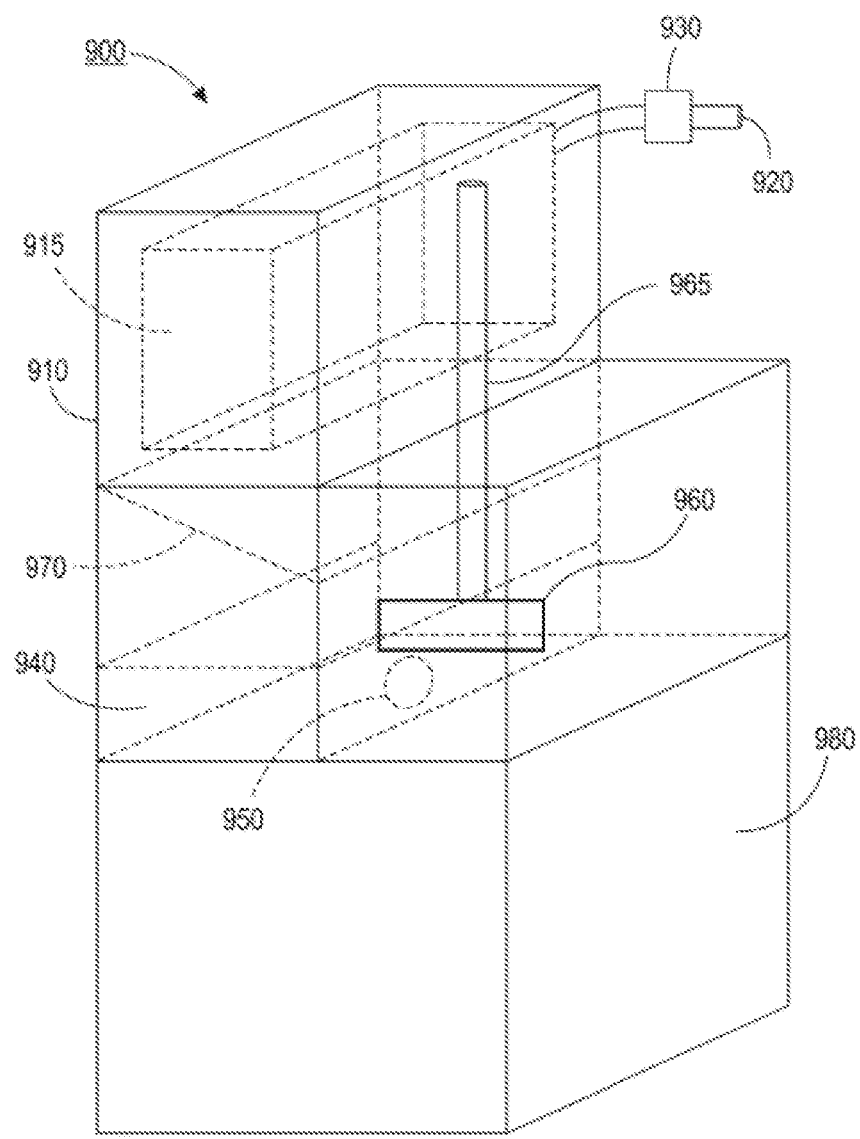
FIG. 9 illustrates a conventional ice making system.

FIG. 9 illustrates a conventional ice making system 900. The ice making system includes an ice producing subsystem 910 that includes an evaporator 915, over which water is distributed by a water distributor (not shown). The water distributor receives water from a sump pump 960 that pumps water, via conduit 965, from a water reservoir or sump 940 to the water distributor. The water reservoir or sump 940 may be prefilled by a water source 920 prior to the ice making process beginning or a water source 920, via valve 930, may provide water directly to the water distributor during the initial stages of the ice making process until the water level in the water reservoir or sump 940 reaches a predetermined level.

During the ice making process, the evaporator 915 become cold, from circulating refrigerant (not shown), such that the water, from the water distributor, freezes as the water interacts with the evaporator 915. Any water not freezing falls to the water reservoir or sump 940 so that the unfrozen water can be recirculated by the sump pump 960, via conduit 965, to the water distributor. The water is recirculated to fall over the evaporator 915 until a predetermined amount of ice is formed.

After the ice is formed, the unused water may be drained from the water reservoir or sump 940, via drain 950. The ice is then released through door 970 and is stored in ice storage bin 980.

An example of a conventional ice making system is disclosed in U.S. Pat. No. 9,003,824. The entire content of U.S. Pat. No. 9,003,824 is hereby incorporated by reference.

Another example of a conventional ice making system is disclosed in Published US Patent Application Number US 2013/03400446 A1. The entire content of US Patent Application Number US 2013/03400446 A1 is hereby incorporated by reference.

A further example of a conventional ice making system is disclosed in Published PCT Patent Application Number WO 2010/048241 A2. The entire content of Published PCT Patent Application Number WO 2010/048241 A2 is hereby incorporated by reference.

Figure 10:
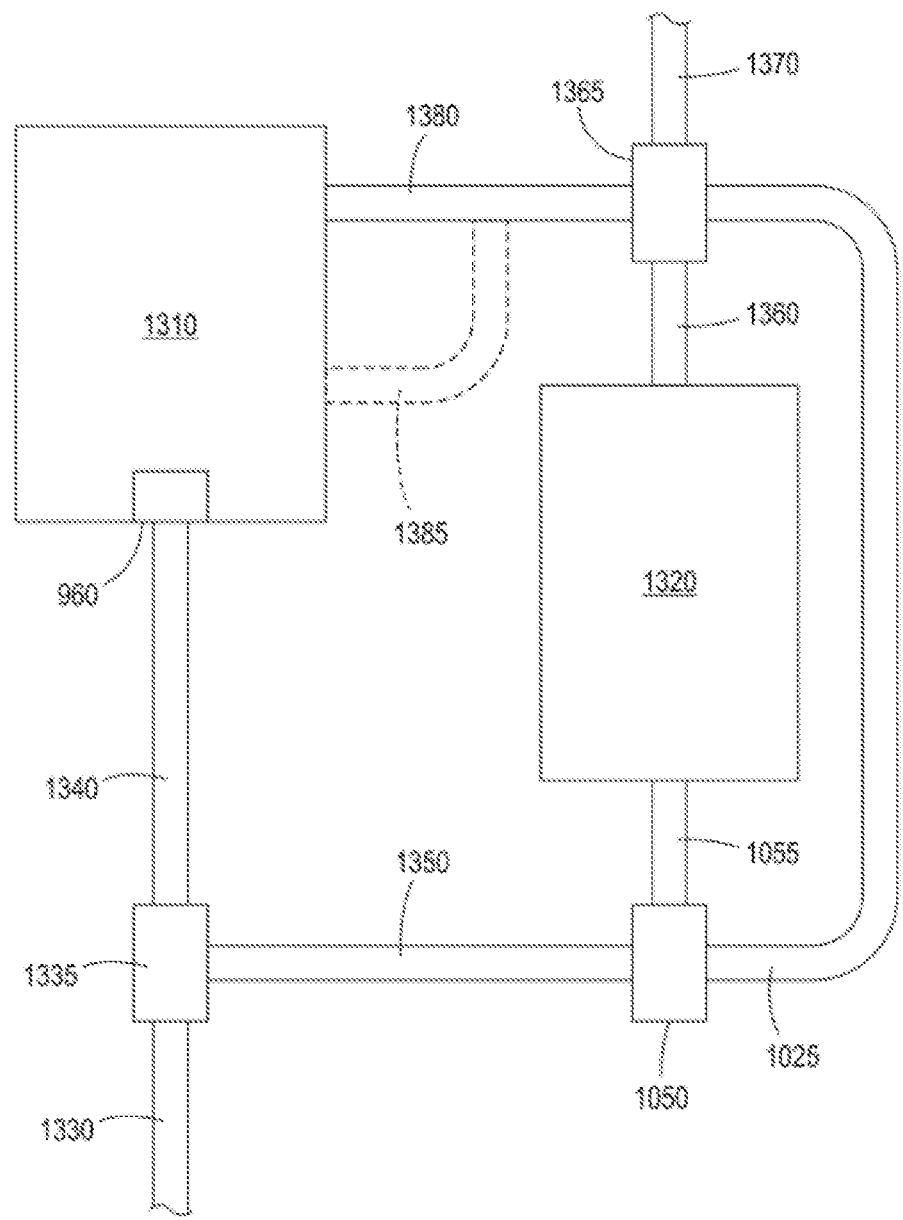
FIG. 10 illustrates a block diagram of an ice making system with recirculating ozonated water sanitizing/cleaning subsystem.

FIG. 10 illustrates a block diagram of an ice making system with recirculating ozonated water sanitizing/cleaning subsystem. As illustrated in FIG. 10, the ice making system includes an ice producing subsystem 1310 that includes a sump/pump system 960. Water, from a water source 1370, is introduced into the ice producing subsystem 1310, via valve 1365 and conduit 1380 or conduit 1385. Conduit 1380 introduces the water to a water distributor associated with an evaporator, and conduit 1385 introduces the water to the sump so that it can be recirculated by sump/pump system 960.

Ozonated water is generated by ozonated water generator 1320. The water that is utilized by the ozonated water generator 1320 is introduced to the ozonated water generator 1320 by the sump/pump system 960, via valve 1335, conduit 1350, valve 1050, and conduit 1055. The water is pumped through the ozonated water generator 1320 and exits as ozonated water, via conduit 1360.

The ozonated water may be introduced into the ice producing subsystem 1310, via valve 1365 and conduit 1380. The ozonated water is then sprayed or dripped throughout the ice producing subsystem 1310 before accumulating in the sump of the ice producing subsystem 1310. The accumulated ozonated water may be recirculated through the ice producing subsystem 1310, or if the cleaning/sanitizing process is complete, the accumulated ozonated water may be expelled, via valve 1335 and drain 1330.

In the ice making process, water is recirculated, via sump/pump system 960, conduit 1340, valve 1335, conduit 1350, valve 1050, conduit 1025, valve 1365, and conduit 1380. If the ice making process is complete, the water may be expelled, via valve 1335 and drain 1330.

It is noted that the ice making system may include a controller to control the various states of the valves and the operations of the ice producing subsystem 1310, sump/pump system 960, and ozonated water generator 1320.

Figure 11:
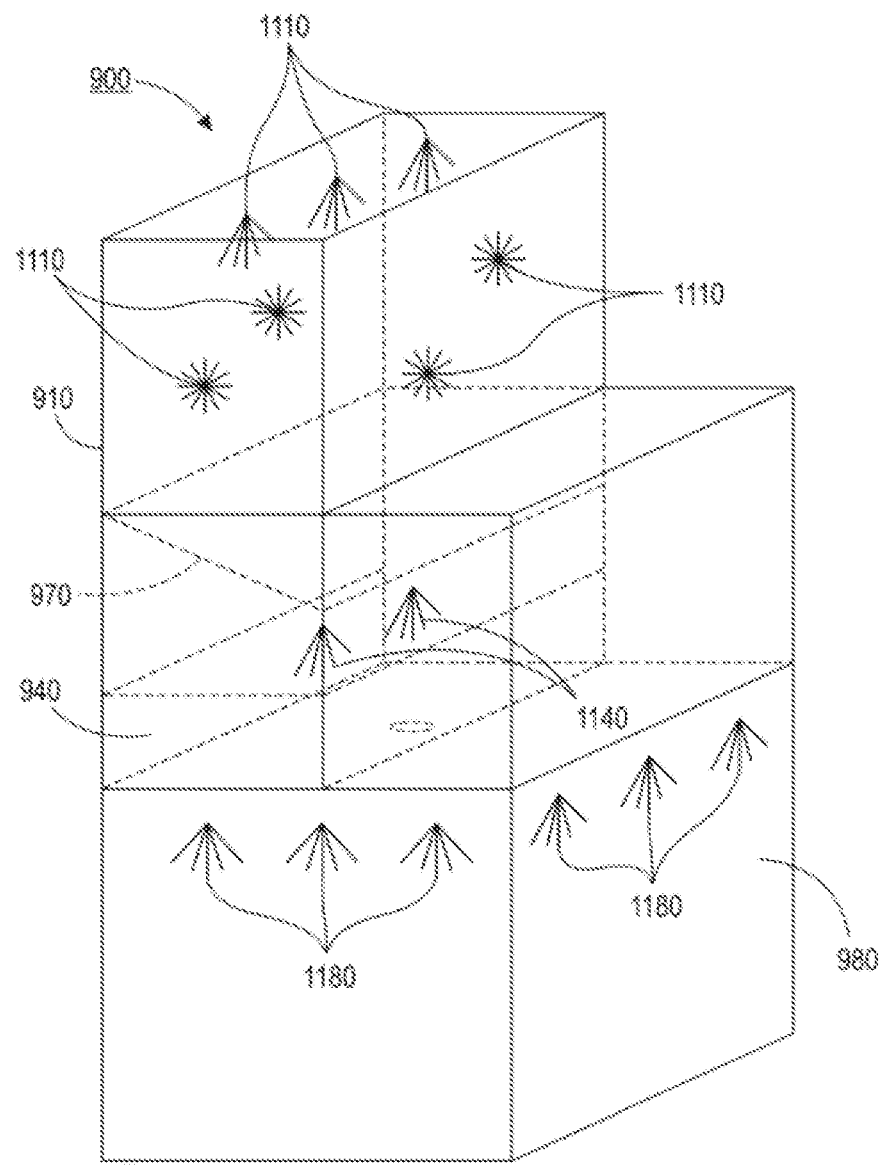
FIG. 11 illustrates the sanitizing/cleaning of an ice making system with sprayed ozonated water.

FIG. 11 illustrates the sanitizing/cleaning of an ice making system 900 with sprayed ozonated water. As illustrated in FIG. 11, an ice producing subsystem 910 is sanitized via ozonated water spray dispensing mechanisms 1110.

The ozonated water spray dispensing mechanisms 1110 may be position throughout the ice producing subsystem 910 so that all the surfaces that contact moisture can be effectively sprayed or doused with ozonated water.

For example, the ozonated water spray dispensing mechanisms 1110 may be co-located with a water distributor to sanitize the water distributor. The ozonated water spray dispensing mechanisms 1110 may be co-located with an evaporator to sanitize the evaporator.

Ozonated water spray dispensing mechanisms 1140 may be co-located with a sump or water reservoir 940 to sanitize the sump or water reservoir.

Ozonated water spray dispensing mechanisms 1180 may be co-located in an ice storage bin 980 to sanitize the ice storage bin. The ozonated water spray dispensing mechanisms 1180 may be orientated so that only walls of the ice storage bin 980 are sprayed so as to minimize the exposure of the ice to the ozonated water. In this way, the ice storage bin 980 can be sanitized without emptying out the ice in the ice storage bin 980.

The ozonated water can also be circulated or recirculated, via a sump pump, through the various conduits and valves to sanitize the remaining components of the ice making system.

Figure 12:
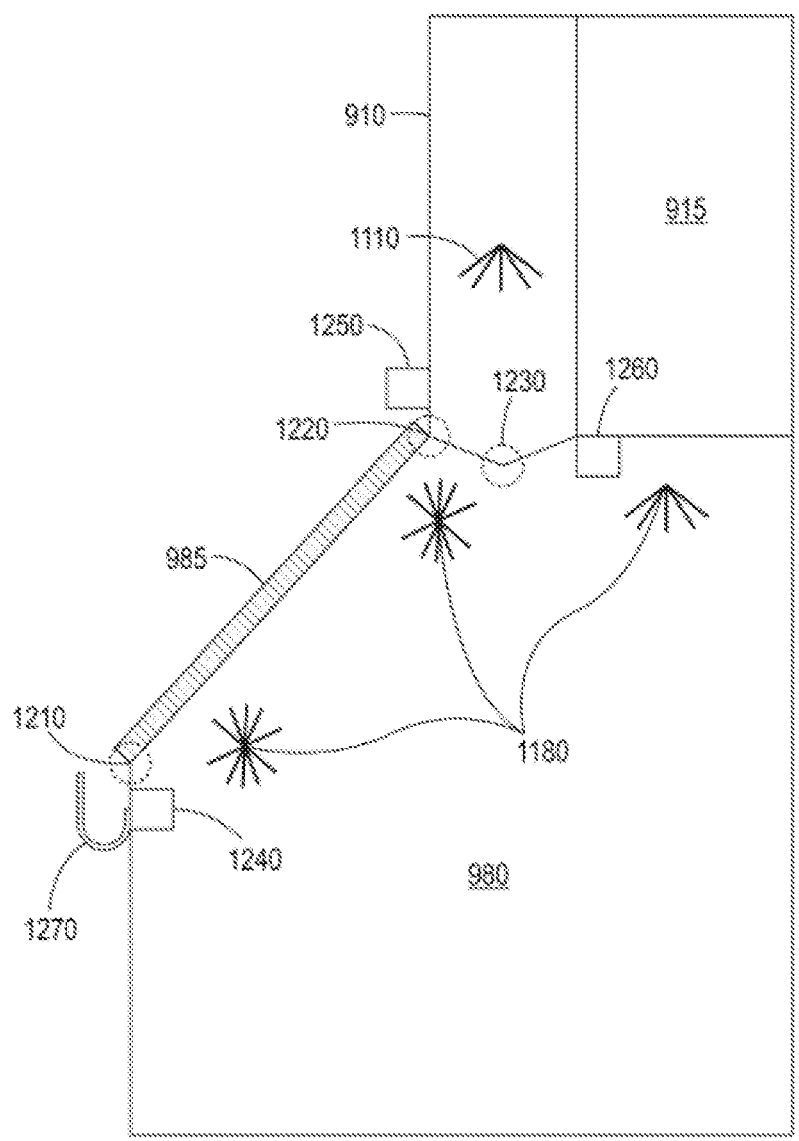
FIG. 12 illustrates the sanitizing/cleaning of various seals in an ice making system with sprayed ozonated water.

FIG. 12 illustrates the sanitizing/cleaning of various seals in an ice making system with sprayed ozonated water. As illustrated in FIG. 12, an ice making system includes an ice producing subsystem 910 having an evaporator 915. The ice making system includes an ice storage bin 980 having a dispensing door 985.

In the ice making system, there are various seals. These seals are areas that can accumulate moisture, and thus, the seals need to be effectively cleaned and/or sanitized.

For example, there may be a seal 1230 associated with a door that allows the ice to be released from the ice producing subsystem 910 and stored in the ice storage bin 980. There also may be seal 1220 and seal 1210 associated with the dispensing door 985 of the ice storage bin 980.

To clean seal 1230, seal 1220, and seal 1210, the ozonated water needs to penetrate the seal without substantially negating the sealed state. To assist the penetration of the ozonated water, each seal has located, in close proximity, a vibrator.

For example, seal 1230 has located, in close proximity, vibrator 1260, which enables the ozonated water from ozonated water spray dispensing mechanisms 1110 to penetrate seal 1230. Vibrator 1260 creates vibrations along seal 1230 to cause a small gap in seal 1230 to enable penetration of the ozonated water.

Seal 1220 has located, in close proximity, vibrator 1250, which enables the ozonated water from ozonated water spray dispensing mechanisms 1180 to penetrate seal 1220. Vibrator 1250 creates vibrations along seal 1220 to cause a small gap in seal 1220 to enable penetration of the ozonated water.

Seal 1210 has located, in close proximity, vibrator 1240, which enables the ozonated water from ozonated water spray dispensing mechanisms 1180 to penetrate seal 1210. Vibrator 1240 creates vibrations along seal 1210 to cause a small gap in seal 1210 to enable penetration of the ozonated water.

The ice making system also includes a channel 1270 located on the outside wall of the ice storage bin 980 to capture any water that penetrates seal 1220 and/or seal 1210. The channel 1270 directs the water to a drain.

Figure 13:
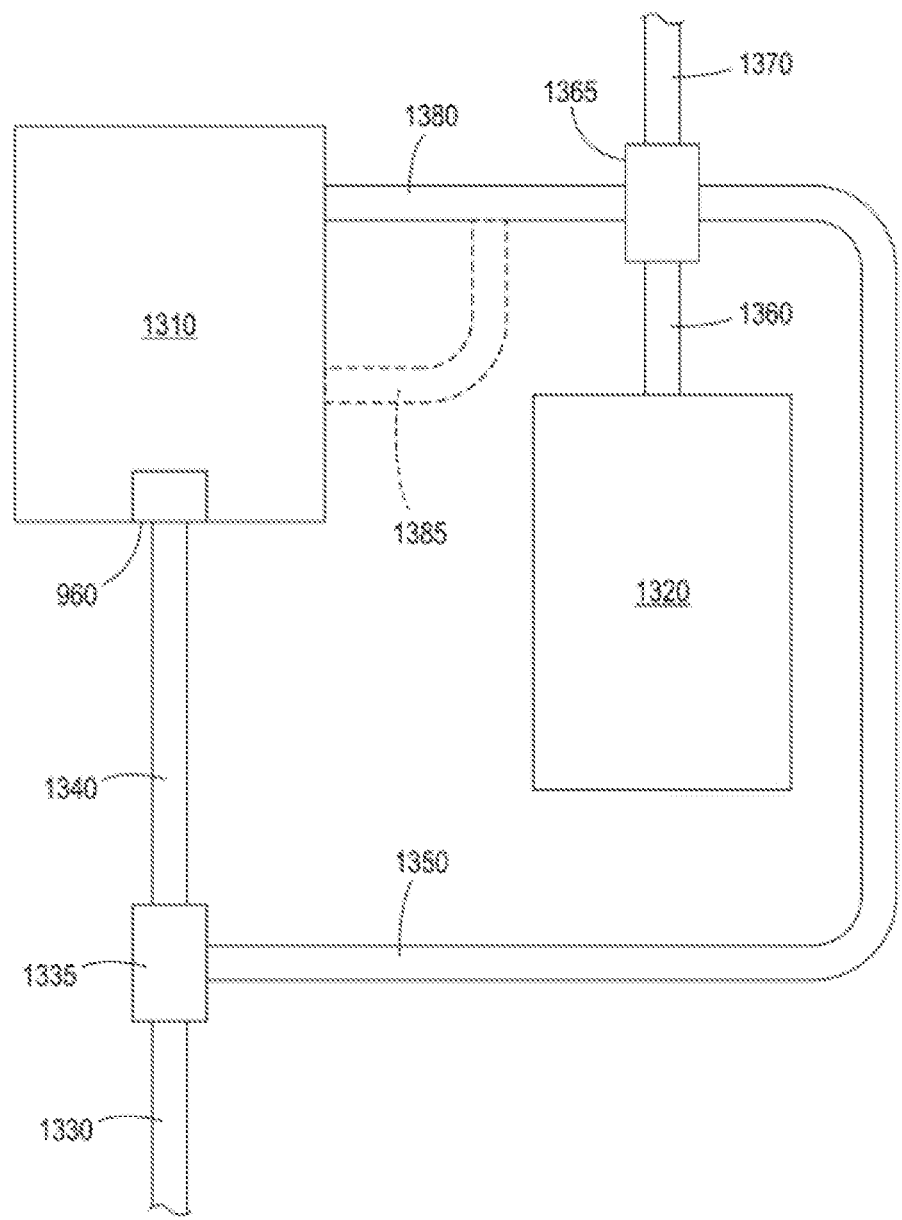
FIG. 13 illustrates a block diagram of an ice making system with non-recirculating ozonated water sanitizing/cleaning subsystem.

FIG. 13 illustrates an ice making system with non-recirculating ozonated water sanitizing/cleaning subsystem. As illustrated in FIG. 13, the ice making system includes an ice producing subsystem 1310 that includes a sump/pump system 960. Water, from a water source 1370, is introduced into the ice producing subsystem 1310, via valve 1365 and conduit 1380 or conduit 1385. Conduit 1380 introduces the water to a water distributor associated with an evaporator, and conduit 1385 introduces the water to the sump so that it can be recirculated by sump/pump system 960.

Ozonated water is generated by ozonated water generator 1320. The ozonated water from the ozonated water generator 1320 exits, via conduit 1360. The ozonated water is introduced into the ice producing subsystem 1310, via valve 1365 and conduit 1380. The ozonated water is then sprayed or dripped throughout the ice producing subsystem 1310 before accumulating in the sump of the ice producing subsystem 1310. The accumulated ozonated water is expelled, via valve 1335 and drain 1330.

In the ice making process, water is recirculated, via sump/pump system 960, valve 1335, conduit 1350, valve 1365, and conduit 1380. If the ice making process is complete, the water may be expelled, via valve 1335 and drain 1330.

It is noted that the ice making system may include a controller to control the various states of the valves and the operations of the ice producing subsystem 1310, sump/pump system 960, and ozonated water generator 1320.

Figure 14:
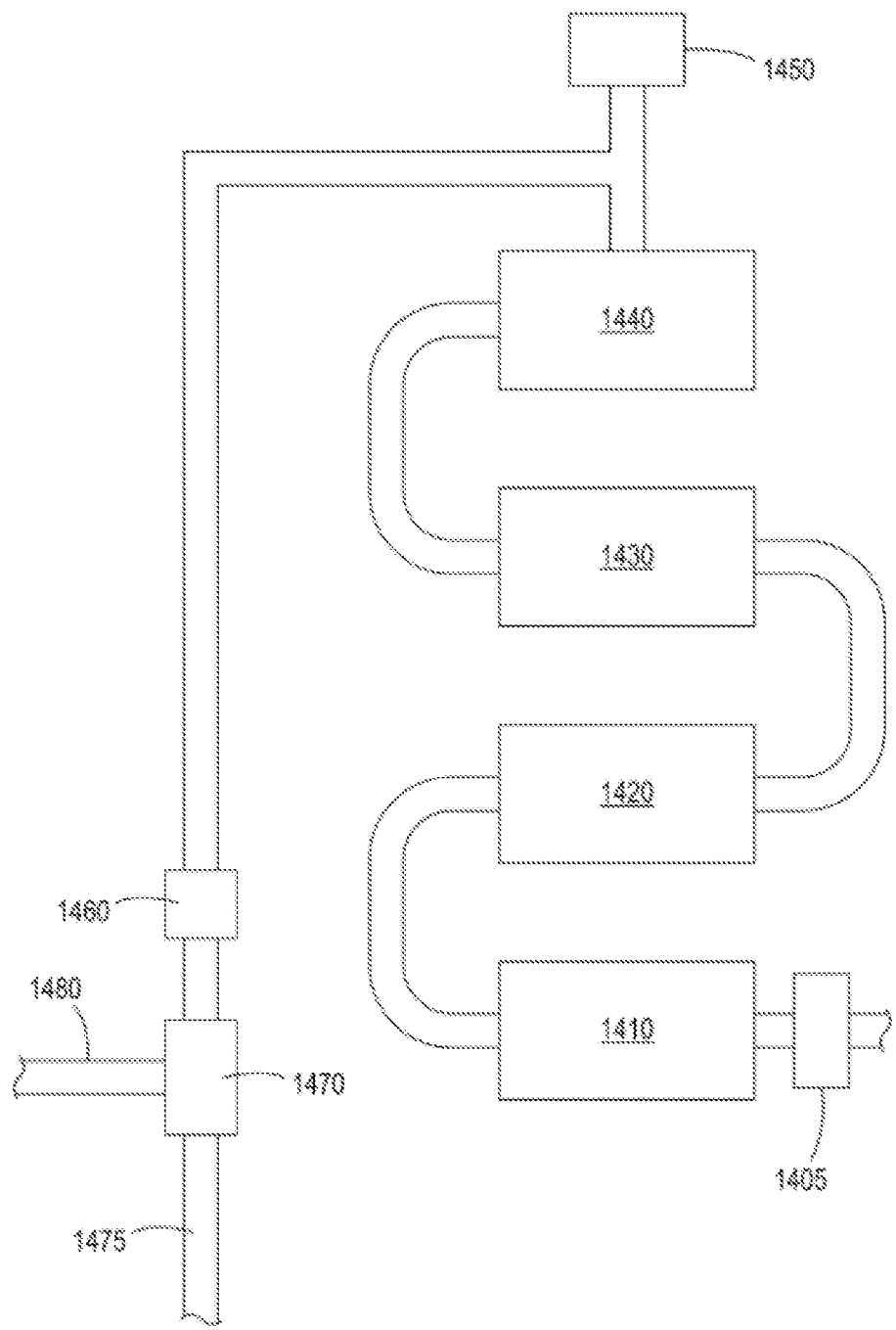
FIG. 14 illustrates an ozonated water generation system.

FIG. 14 illustrates an ozonated water generation system. As illustrated in FIG. 14, the ozonated water generation system includes multiple ozonated water generators (1410, 1420, 1430, and 1440) connected in series. It is noted that the number of ozonated water generators connected in series may be any number. In this configuration, all the ozonated water generators may be simultaneously operational or only a portion of them, depending upon the demand for ozonated water generation.

For example, if the demand for ozonated water generation is high, ozonated water generators (1410, 1420, 1430, and 1440) may be simultaneously operational. On the other hand, if the demand for ozonated water generation is low, ozonated water generator 1410 may be the only ozonated water generator that is operational.

The ozonated water generators (1410, 1420, 1430, and 1440) may be electrolytic ozone generators.

As the ozonated water leaves the last ozonated water generator 1440, the ozone gas generated during ozonated water generation is vented by automatic air eliminator and air purger 1450. The ozonated water is circulated to an oxidation-reduction potential sensor 1460 which measures the amount (ppm) of ozone in the water. The oxidation-reduction potential sensor 1460 can regulate the strength of the ozonated water, via bypass valve 1470 and/or flow regulator 1405.

For example, if the desired strength of the ozonated water is 1.5 ppm and the strength of the ozonated water is below 1.5 ppm, the oxidation-reduction potential sensor 1460, in conjunction with a controller, may cause the bypass valve 1470 to divert the water to a drain 1475 until the ozonated water is 1.5 ppm. Once the ozonated water is 1.5 ppm, the oxidation-reduction potential sensor 1460, in conjunction with a controller, causes the bypass valve 1470 to divert the water to conduit 1480 for use in a sanitizing operation.

On the other hand, if the desired strength of the ozonated water is 1.5 ppm and the strength of the ozonated water is below 1.5 ppm due to a non-functioning ozonated water generator, the oxidation-reduction potential sensor 1460, in conjunction with a controller, may cause the bypass valve 1470 to divert the water to a drain 1475 and the water volume through the flow regulator 1405 to decrease until the ozonated water is 1.5 ppm. Once the ozonated water is 1.5 ppm, the oxidation-reduction potential sensor 1460, in conjunction with a controller, causes the bypass valve 1470 to divert the water to conduit 1480 for use in a sanitizing operation.

It is noted that once the ozonated water is 1.5 ppm, the oxidation-reduction potential sensor 1460, in conjunction with a controller, may cause one or more of the ozonated water generators to become non-operational (since ozonated water has a shelf life) until the oxidation-reduction potential sensor 1460 senses the strength of the ozonated water is below 1.5 ppm.

It is also noted that the ppm strength (concentration) of the ozonated water may be a concentration other than 1.5 ppm.

The ozonated water can be used to clean and/or sanitize an ice making machine or other food service equipment; such as smoothie machines, blenders, hoses, beer taps, and/or drink dispensers. The ozonated water can be used to clean and/or sanitize bathrooms, an employee's hands, raw food, vegetables, fruit, and/or the surfaces, tools, or utensils that are used in processing raw food, vegetables, and/or fruit.

Figure 15:
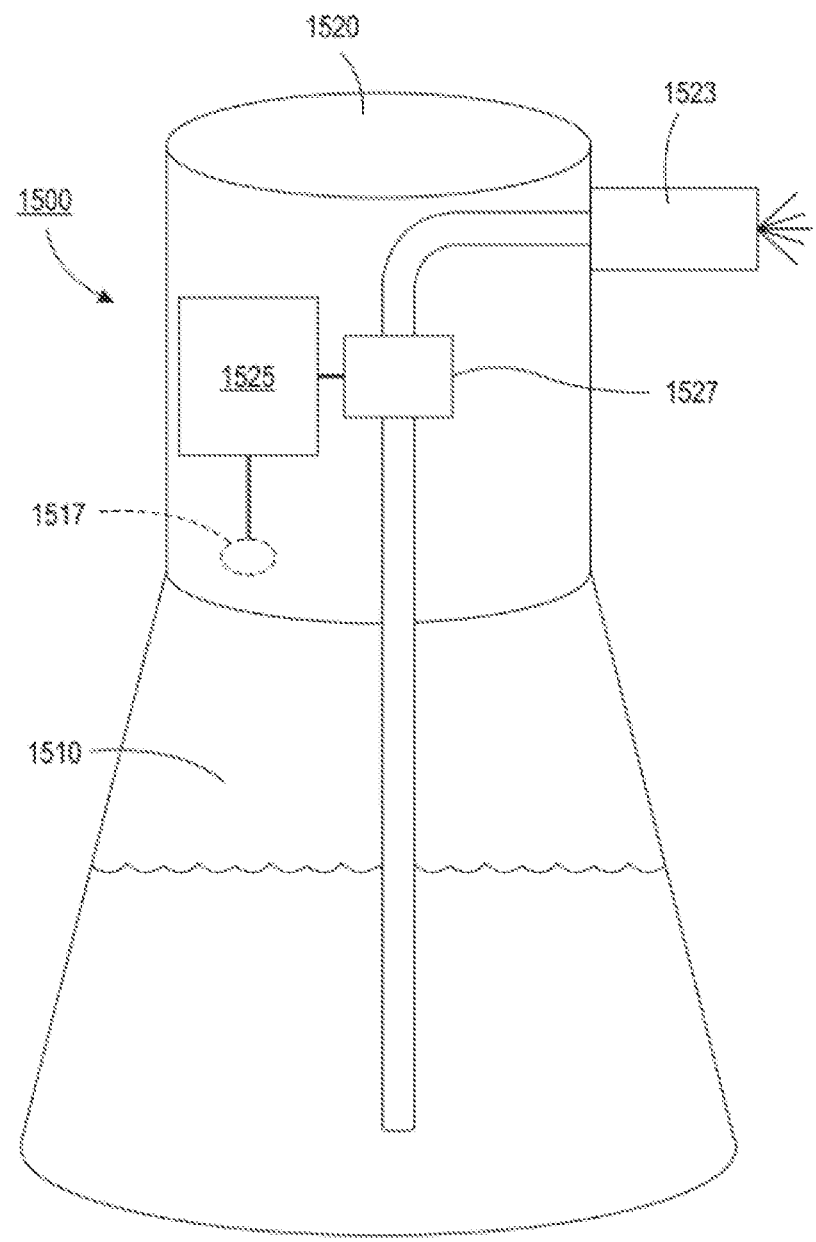
FIG. 15 illustrates an ozonated water cleaning device of a cleaning monitoring system.

FIG. 15 illustrates an ozonated water cleaning device of a cleaning monitoring system. As illustrated in FIG. 15, an ozonated water cleaning device 1500 includes an ozonated water reservoir 1510 and a dispensing mechanism 1520. The dispensing mechanism 1520 includes a spray dispensing device 1523, a controller (microprocessor) 1525, and pump 1527. The pump 1527 may be motorized that is driven by an ON button 1517 or a mechanical pump driven by the mechanical actions of a user.

Since ozonated water has an effective shelf life, the controller (microprocessor) 1525 monitors the time that effective ozonated water is in the ozonated water reservoir 1510. If the time that the effective ozonated water is in the ozonated water reservoir 1510 is greater than the effective shelf life, the controller (microprocessor) 1525 can disable the pump 1527 so that the ineffective ozonated water is not dispensed. The dispensing of ineffective ozonated water will not effectively clean or sanitize and thus give the operator a false understanding of the sanitized state of the item being cleaned or sanitized.

The controller (microprocessor) 1525, via appropriate sensors (not shown), can determine the replacement of the water in the ozonated water reservoir 1510, thereby re-enabling the operation of the pump 1527.

The controller (microprocessor) 1525, via appropriate sensors (not shown), can monitor the amount of effective ozonated water that is dispensed. The controller (microprocessor) 1525, via an appropriate transceiver (not shown), can determine the area or item being cleaned and the amount of effective ozonated water that is dispensed.

This information can be communicated by the controller (microprocessor) 1525, via an appropriate transceiver (not shown), to a monitoring system to track the cleaning of various areas and/or items.

Figure 16:
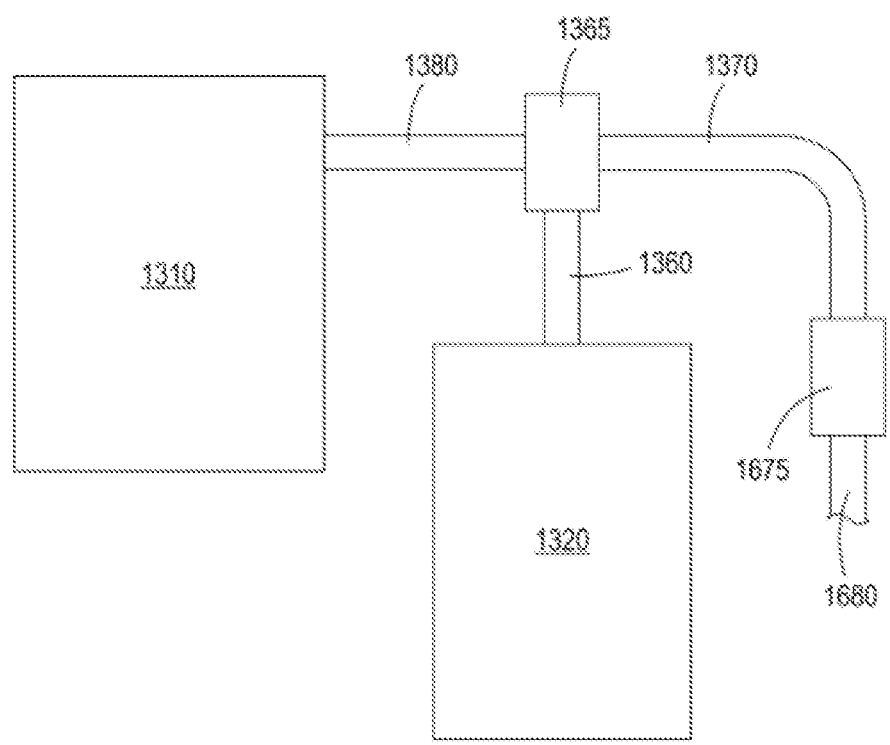
FIG. 16 illustrates a block diagram of another ice making system with non-recirculating ozonated water sanitizing/cleaning subsystem.

FIG. 16 illustrates another ice making system with non-recirculating ozonated water sanitizing/cleaning subsystem. As illustrated in FIG. 16, the ice making system includes an ice producing subsystem 1310. Ozonated water is generated by ozonated water generator 1320. The ozonated water from the ozonated water generator 1320 exits, via conduit 1360.

The ozonated water is introduced into the ice producing subsystem 1310, via an automatic air eliminator and air purger/valve system 1365 and conduit 1380. The ozonated water is then sprayed or dripped throughout the ice producing subsystem 1310 before accumulating in the sump of the ice producing subsystem 1310.

The automatic air eliminator and air purger/valve system 1365 vents the gaseous ozone via conduit 1370 to a catalytic converter 1675, which converts the ozone gas to oxygen gas, which is vented through conduit 1680. The catalytic converter 1675 may be a Carulite™ catalytic converter.

It is noted that since ozone is a heavier than air, the catalytic converter 1675 can be located below the automatic air eliminator and air purger/valve system 1365 so that gravity causes the ozone to pass through the catalytic converter 1675.

Figure 17:
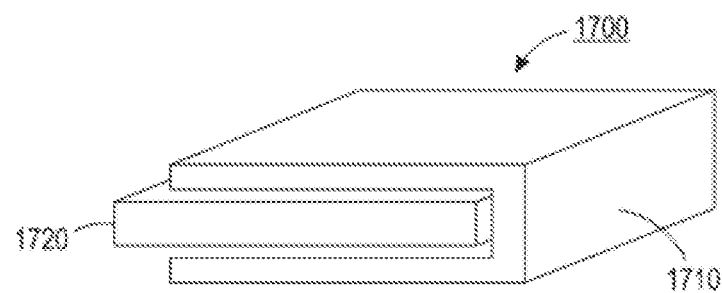
FIGS. 17 and 18 illustrate an electrolytic ozone generator.
Figure 18:
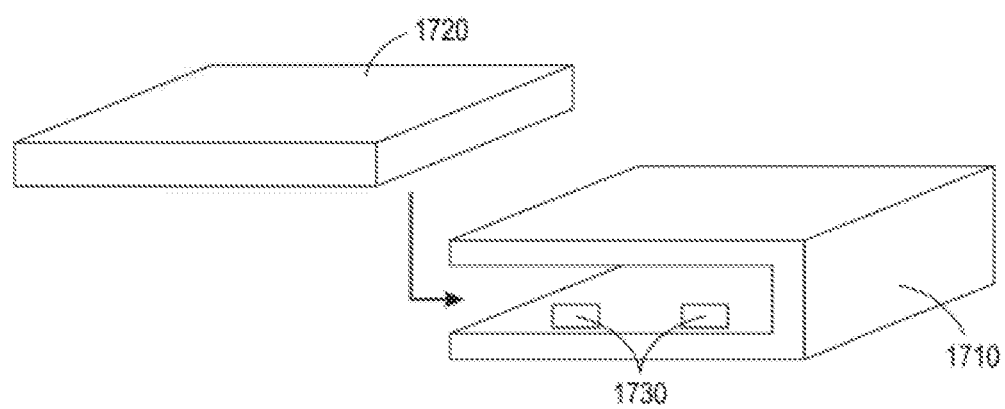

FIGS. 17 and 18 illustrate an electrolytic ozone generator. As illustrated in FIG. 17 the electrolytic ozone generator 1700 is a three layer device having a titanium anode 1720, a U-shaped or C-Shaped cathode 1710, and insulators 1730 (FIG. 18). During operations, the titanium anode 1720 is located within the U-shaped or C-Shaped cathode 1710.

If the electrolytic ozone generator 1700 wears out, as illustrated in FIG. 18, the U-shaped or C-Shaped cathode 1710 can be easily replaced with a new U-shaped or C-Shaped cathode 1710 and reusing the titanium anode 1720.

Figure 19:
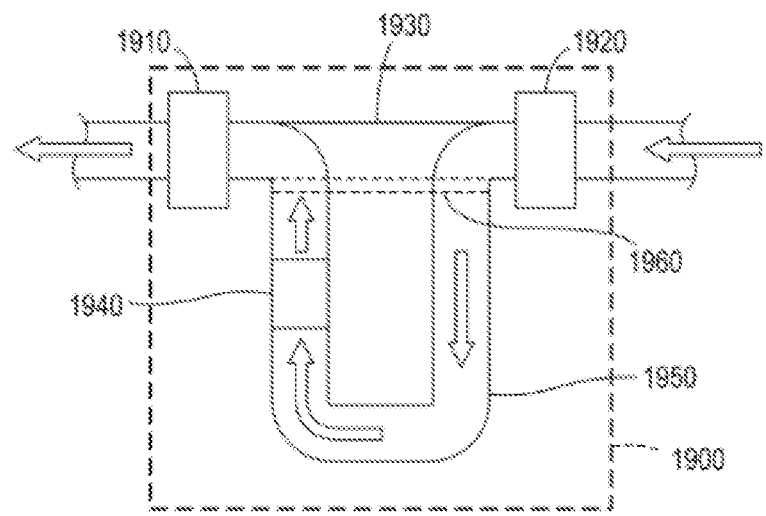
FIG. 19 illustrates an ozonated water generator.

FIG. 19 illustrates an ozonated water generator. As illustrated in FIG. 19, the ozonated water generator 1900 includes an ozone generator 1940. The ozonated water generator 1900 has a top portion 1930 and a bottom portion 1950. The top portion 1930 and the bottom portion 1950 are detachable from each other at connection area 1960. The connection area 1960 may be a threaded area with the appropriate O-ring to provide a proper connection and water tight seal between the top portion 1930 and the bottom portion 1950.

The top portion 1930 includes couplers 1910 and 1920 to connect the ozonated water generator 1900 to either a conduit or another ozonated water generator. Water enters the top portion 1930 through coupler 1920 and is diverted to the bottom portion 1950. The bottom portion 1950 routes the water to the ozone generator 1940 before being routed to the top portion 1930. The water passing over the ozone generator 1940 is ozonated. The ozonated water exits the top portion 1930 through coupler 1910.

As noted above, an ozonated water generation system may include multiple ozonated water generators connected in series. By utilizing multiple ozonated water generators connected in series, the water is ozonated multiple times as it traverses from one ozonated water generator to another ozonated water generator.

Also, utilizing multiple ozonated water generators connected in series, the number of ozonated water generators actually operational can be controlled to meet the demand for ozonated water.

For example, as the demand increases, more ozonated water generators can be become operational, or as the demand decreases, less ozonated water generators are operational.

In addition, utilizing multiple ozonated water generators connected in series, the number of ozonated water generators in the ozonated water generation system may be more than actually needed so that when an ozonated water generator becomes non-functional, there are enough redundant ozonated water generators to make the necessary ozonated water until the non-functional ozonated water generator can be replaced or repaired.

Figure 20:
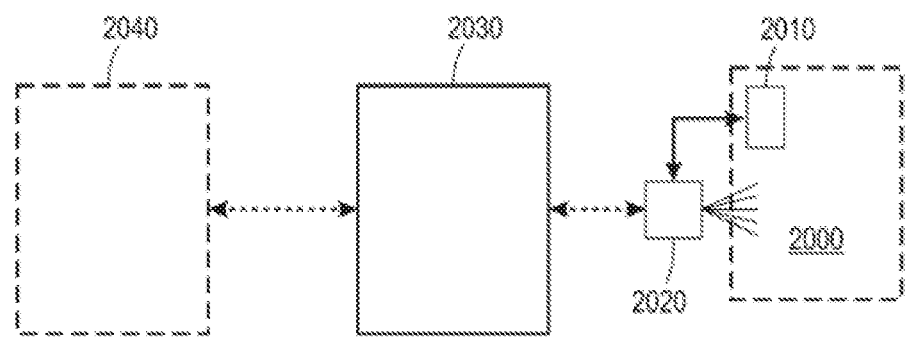
FIG. 20 illustrates a block diagram of a cleaning monitoring system.

FIG. 20 illustrates a cleaning monitoring system. As illustrated in FIG. 20, an ozonated water cleaning device 2020 communicates, via a RFID tag 2010, with an area 2000 to be cleaned. The RFID tag 2010 identifies the area being cleaned.

As discussed above, ozonated water cleaning device 2020, via an appropriate transceiver (not shown), communicates to a local monitoring system 2030 to track the cleaning of various areas and/or items. The local monitoring system 2030 can optionally communicate the cleaning information to a remote (corporate) monitoring system 2040 to track the cleaning procedures of various locations.

Figure 21:
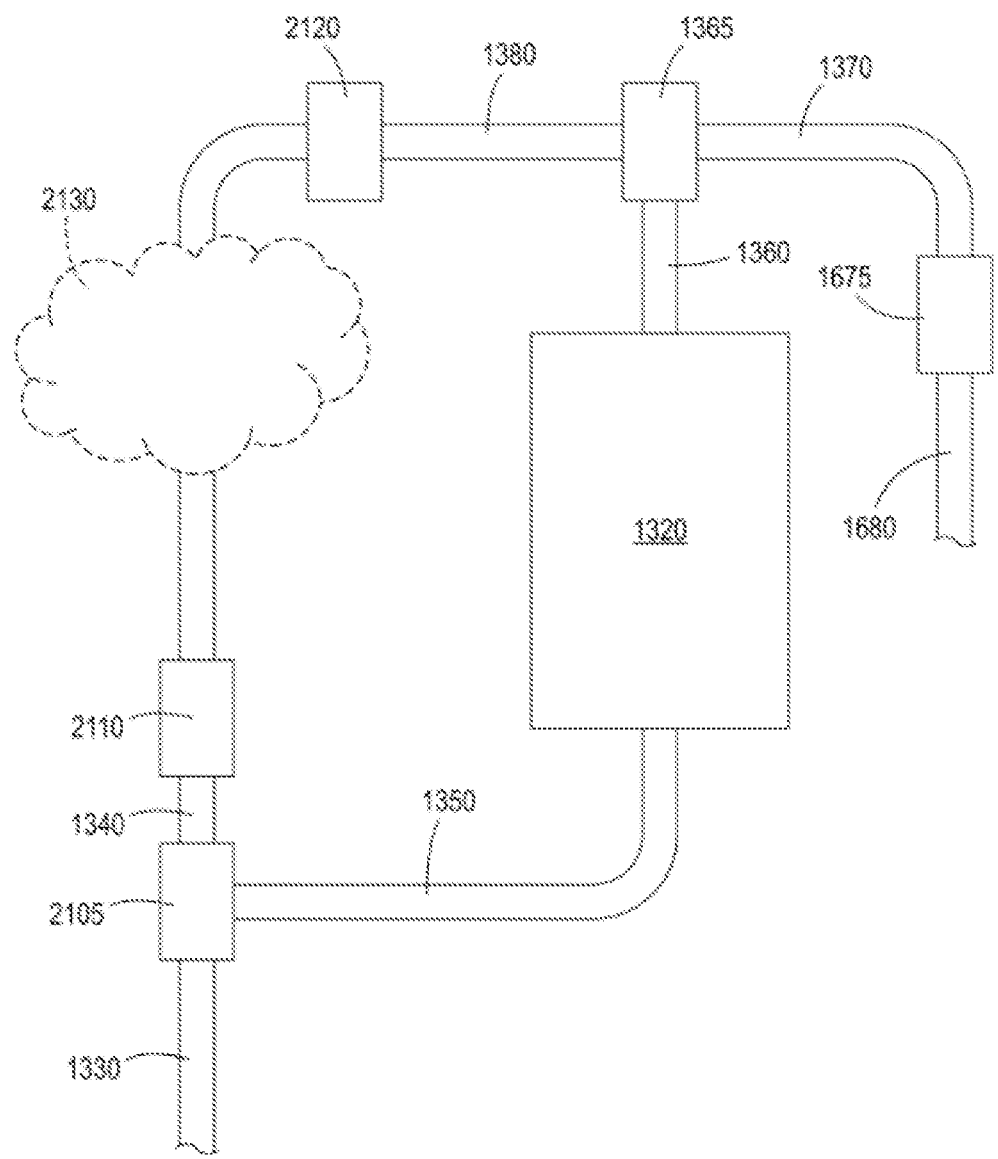
FIG. 21 illustrates a block diagram of an ozonated water generation system.

FIG. 21 illustrates an on-demand ozonated water generation system. As illustrated in FIG. 21, ozonated water from ozonated water generator 1320 exits, via conduit 1360. The ozonated water is introduced into on-demand ozonated water dispensing system 2130, via an automatic air eliminator and air purger/valve system 1365, conduit 1380, and oxidation-reduction potential sensor 2120.

The ozonated water is circulated to the oxidation-reduction potential sensor 2120 which measures the amount (ppm) of ozone in the water. The oxidation-reduction potential sensor 2120 can regulate the strength of the ozonated water, via bypass valves (not shown) and/or flow regulators (not shown).

For example, if the desired strength of the ozonated water is 1.5 ppm and the strength of the ozonated water is below 1.5 ppm, the oxidation-reduction potential sensor 2120, in conjunction with a controller, may cause a bypass valve (not shown) to divert the water to a drain (not shown) until the ozonated water is 1.5 ppm. Once the ozonated water is 1.5 ppm, the oxidation-reduction potential sensor 2120, in conjunction with a controller, causes a bypass valve (not shown) to divert the water to on-demand ozonated water dispensing system 2130 for use in a sanitizing operation.

On the other hand, if the desired strength of the ozonated water is 1.5 ppm and the strength of the ozonated water is below 1.5 ppm due to a non-functioning ozonated water generator, the oxidation-reduction potential sensor 2120, in conjunction with a controller, may cause a bypass valve (not shown) to divert the water to a drain (not shown) and the water volume through a flow regulator (not shown) to decrease until the ozonated water is 1.5 ppm.

Once the ozonated water is 1.5 ppm, the oxidation-reduction potential sensor 2120, in conjunction with a controller, causes a bypass valve (not shown) to divert the water to on-demand ozonated water dispensing system 2130 for use in a sanitizing operation.

It is noted that once the ozonated water is 1.5 ppm, the oxidation-reduction potential sensor 2120, in conjunction with a controller, may cause one or more of the ozonated water generators to become non-operational (since ozonated water has a shelf life) until the oxidation-reduction potential sensor 2120 senses the strength of the ozonated water is below 1.5 ppm. It is also noted that the ppm strength (concentration) of the ozonated water may be a concentration other than 1.5 ppm.

The automatic air eliminator and air purger/valve system 1365 vents the gaseous ozone via conduit 1370 to a catalytic converter 1675, which converts the ozone gas to oxygen gas, which is vented through conduit 1680. The catalytic converter 1675 may be a Carulite™ catalytic converter.

It is noted that since ozone is a heavier than air, the catalytic converter 1675 can be located below the automatic air eliminator and air purger/valve system 1365 so that gravity causes the ozone to pass through the catalytic converter 1675.

The on-demand ozonated water generation system also includes a pump 2110 to recirculate the ozonated water, via conduit 1340, valve 2105, and conduit 1350. If the on-demand ozonated water generation system requires additional water, the water is introduced via conduit 1330 and valve 2105.

The on-demand ozonated water dispensing system 2130 may divert ozonated water to an ice making system, a fluid dispensing system, a hand cleansing device, a device for dispensing the ozonated water into portable cleaning devices, etc.

With respect to FIG. 21, instead of putting an ozonated water generator inside an ice machine and spraying to clean the ice machine, FIG. 21 utilizes multiple ozonated water generators at a central location and utilizes a recirculated line all around a location (restaurant) to dispense the ozonated water at multiple locations.

An advantage of ozonated water is that it can be sprayed on food without ruining the food like chlorine, thus, items can be sanitized multiple times daily without interrupting food production in a restaurant.

In an on-demand ozonated water dispensing system in conjunction with a monitoring system, when an employee wants to take a bottle of ozonated water to go spray the tables somewhere, the employee fills bottle with ozonated water. This sets a timer inside the spray bottle so the electric pump is shut off in about fifteen minutes, which is before the ozonated water losses effectiveness.

As previously described, the sprayer can be equipped with an RFID reader, and RFID chips (tags) can be placed around the location. As the employee cleans various locations, the RFID reader recognizes and records the time and place along with the age of the ozonated water. Then when the bottle is placed back on a rack, the information can be uploaded to a central monitoring location where cleaning can be centrally monitored and warnings communicated if the cleaning is not done properly.

Figure 22:
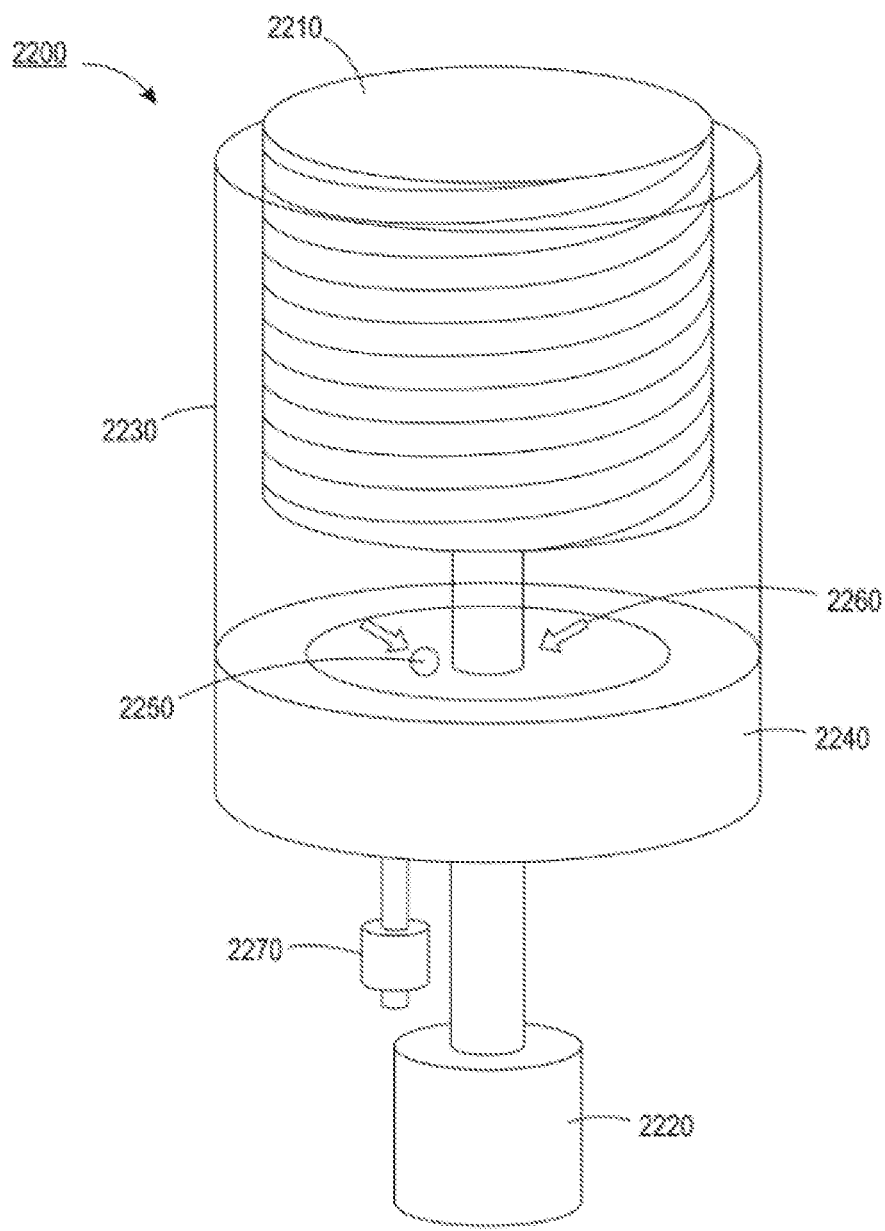
FIG. 22 illustrates a placement of a drain for a nugget ice making machine.

FIG. 22 illustrates a drain location for an evaporator/auger/cylinder nugget ice making machine 2200. Examples of an evaporator/auger/cylinder nugget ice making machine are disclosed in U.S. Pat. Nos. 7,469,548; 8,756,950; and Published US Patent Application Number 2016/0003515. The entire contents of U.S. Pat. No. 7,469,548; US Pat. No. 8,756,950; and Published US Patent Application Number 2016/0003515 are hereby incorporated by reference.

As illustrated in FIG. 22, the evaporator/auger/cylinder nugget ice making machine 2200 includes an auger 2210 driven by motor 2220. The auger 2210 is located within a cylinder 2230. The cylinder 2230 includes an end cap 2240, which includes a drain 2250.

The drain 2250 is located at the lowest point of the interior surface of the evaporator/auger/cylinder nugget ice making machine 2200 such that all the water flows 2260 towards this low point (drain 2250). The drain 2250 is connected with a drain valve 2270.

The end cap 2240 may be contoured so that the interior surface slopes towards the drain 2250 without or with minimal obstructions.

FIG. 22 shows the evaporator/auger/cylinder nugget ice making machine 2200 being in a vertical orientation; however, the evaporator/auger/cylinder nugget ice making machine 2200 may be in a horizontal orientation. When in the horizontal orientation, the drain 2250 is located such that the drain 2250 is at the lowest point of the interior surface of the evaporator/auger/cylinder nugget ice making machine 2200. It is noted that by slightly titling the evaporator/auger/cylinder nugget ice making machine 2200, when in the horizontal orientation, assists the mineralized water accumulating at the lowest point (drain 2250).

In such a system, minerals (such as calcium) accumulate, during the ice making process, at the lowest point. Thus, by briefly opening the drain valve 2270, at the end of the ice making process, the mineralized water can be removed by gravity without requiring a flush with water. The brief opening of the drain valve 2270 and the drain 2250 being located at the lowest point of the interior surface of the evaporator/auger/cylinder nugget ice making machine 2200 allows the mineralized water to be removed by gravity without requiring a flush with water.

Figure 23:
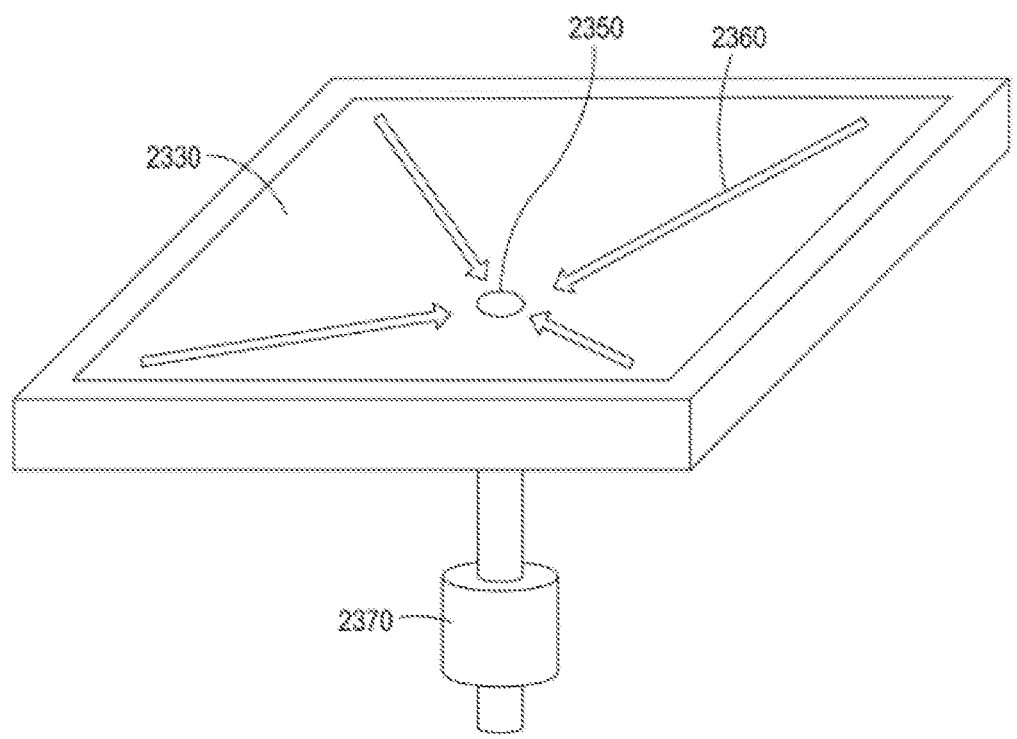
FIG. 23 illustrates a placement of a drain for a water sump of an ice making machine.

FIG. 23 illustrates a drain location for water sump 2330 for the various ice making machines discussed above. As illustrated in FIG. 23, the water sump 2330 includes a drain 2350. The drain 2350 is located at the lowest point of the water sump 2330 such that all the water flows 2360 towards this low point (drain 2350). The drain 2350 is connected with a drain valve 2370.

The water sump 2330 may be contoured so that the surface slopes towards the drain 2350 without or with minimal obstructions.

In such a system, minerals (such as calcium) accumulate, during the ice making process, at the lowest point. Thus, by briefly opening the drain valve 2370, at the end of the ice making process, the mineralized water can be removed by gravity without requiring a flush with water. The brief opening of the drain valve 2370 and the drain 2350 being located at the lowest point of the water sump 2330 allows the mineralized water to be removed by gravity without requiring a flush with water.

By spraying surfaces down with ozonated water approximately every twenty-four hours, the ozonated water can prevent any colonization of mold and therefore eliminate the need to physically clean for caked up mold and slime.

It is noted that the spraying of the surfaces with ozonated water should be realized during a non-ice making process so that ozonated ice is not inadvertently made and mixed with the non-ozonated ice. Although ozonated ice is not typically harmful, ozonated ice has the taste of ozone, which is not desirable. Moreover, in a hospital environment, ozonated ice is not acceptable because the ozone in the ice is an active ingredient and cannot be given to patients.

Thus, during a non-ice making process, ozonated water is sprayed over the ice making subsystem, including the evaporator, and is collected in the water sump. A pump can then recirculate, for a predetermined period of time (e.g. ten minutes), the ozonated water through the various conduits, valves, and/or distributors of the ice making subsystem.

At the end of the cleaning routine, the ozonated water is flushed (drained) from the ice making subsystem and non-ozonated water is added to the ice making subsystem for the next ice making process.

The above described ozonated water cleaning system can be easily added to an existing ice making machine. Initially the existing ice making machine is cleaned of all slime and mold. Thereafter, the existing ice making machine can be retrofitted with an ozonated water generation system and the spraying system, as described above. The retrofit would also include a controller or control box that would sense when the ice making process has completed, thereby turning OFF the ice making machine.

Upon turning OFF the ice making machine, the controller or control box causes the ozonated water from the ozonated water generation system to be delivered (pumped) to the spraying system within the ice making machine. Upon completion of the spray (cleaning) cycle, the controller or control box causes the ozonated water to be drained from the ice making machine and the ice making machine turned back ON, thereby restarting the ice making process after the cleaning process is completed.

It is noted that the controller or control box turning ON the ice making machine triggers a startup program which causes the existing water (ozonated water) to be flushed or drained, and new water added for the next ice making cycle.

In another embodiment of an ozonated water cleaned ice machine, ozonated water sprayers are located inside the ice machine so the ozonated water spray contacts all the surfaces that may become moist during normal operation and therefore attract airborne microorganisms.

Ozonated water is also pumped into the incoming water line or into the float valve reservoir or water tray so that the ice machine can start to make ice with ozonated water. The ozonated water in the float valve reservoir is used to make ice but discontinues making ice just before the ice is ready for release to the ice storage bin.

To prevent the consumption of frozen ozonated ice, just before the frozen ozonated ice is dropped in the ice storage bin, the ice machine is turned OFF, the drain/dump valve is opened, and ozonated water is sprayed into the top of the evaporator to melt the ice. The sprayers also spray into the ice storage bin to clean/sanitize the ice storage bin walls and stirrer.

The ozonated water that is sprayed into the top of the evaporator also helps remove concentrated calcium and salts because the concentrated calcium and salts are sent down the drain rather than collecting on the bottom of the evaporator.

One example of cleaning an ice making machine utilizes the following procedure.

Initially, the ice making process of the ice making machine is turned OFF and all water, which had been used to create the ice, is drained from the machine. Thereafter, the ice machine, can, optionally, be sprayed, using the ozonated water spraying devices described above, to wash away any dirt, concentrated minerals (such as calcium), and partially frozen ice. The water used in this rinsing process is drained from the machine.

If the cleaning process is a recirculating process, the water reservoir is filled with ozonated water from the ozonated water generation system. The ozonated water is then re-circulated throughout the ice making machine, via a pump, such that the ozonated water is sprayed onto surfaces of the ice making machine which are susceptible to micro-organism growth and/or scale. The pump remains ON a predetermined amount of time (about ten to fifteen minutes because the ozonated water is only effective for about twenty minutes) to insure that the ice making machine is properly sanitized. Thereafter, the used ozonated water is drained from the ice making machine, and the ice making process of the ice making machine is turned ON.

If the cleaning process is non-recirculating process, ozonated water is pumped directly from the ozonated water generation system and into the distribution system so that the ozonated water is sprayed onto surfaces of the ice making machine which are susceptible to micro-organism growth and/or scale. The pump remains ON a predetermined amount of time to insure that all surfaces have been adequately saturated with ozonated water to properly sanitize the ice making machine. During the process, the used ozonated water is drained from the ice making machine. Once the pumping is terminated and the ozonated water has been drained, the ice making process of the ice making machine is turned ON.

It is noted that if the ice making machine includes an ice storage bin, the ice storage bin is cleaned with the ozonated water without emptying the ice from the bin. The ice storage bin is not included in the optional water rinse procedure.

As noted above, the ozonated water spraying devices are located throughout all the "food" zones and splash zones; i.e., any area that is exposed to the ice, water, or may collect moisture from the ice making process.

It is further noted that the ozonated water spraying devices may be utilized by a de-scaling system, wherein de-mineralized water is pumped through the distribution system, and the de-mineralized water is sprayed on the various surfaces to prevent scale buildup. It is noted that the de-mineralized water is not necessarily sprayed in the ice storage bin due to lack of scale buildup in this area.

The above described water spraying devices may be conventional sprayers or nozzles. It is also noted that the above described water spraying devices may provide a dripping action instead of a spraying action.

By utilizing ozonated water during the sanitizing cycle, the sidewalls of an ice storage bin can be properly cleaned with the ice remaining in the storage bin. The ozonated water is safe and leaves no residue.

In another embodiment, an ice machine prevents scale by evacuating all the mineral laden water through a drain. After all the concentrated mineralized water from the ice making process is drained, sprayers are activated with water to wash or drive any residual sediment down the drain.

The drain is then closed and water partially fills a water tray or reservoir, and a sump pump is turned ON to pump the water in a recirculating circuit. This process cleans the tray, the pump, and the drain with water by washing the majority of the harmful scale causing minerals down the drain.

However, due to surface tension, droplets of water remain on all these surfaces which will turn into scale as the water evaporates. Therefore, the sprayers are switched to a mineral free water source and the same process of spraying down the water tray or water reservoir, the drain, and the pump is repeated. This leaves the various parts clean of minerals so that when the mineral free water dries, it does not leave a mineral deposit.

In summary, sanitizing system for ice storage equipment includes an ice storage bin and an ozonated water generator to create ozonated water. The ice storage bin includes a bottom, a plurality of sidewalls, and an ice receiving inlet. The plurality of sidewalls are disposed substantially perpendicular to the bottom of the ice storage bin to create an interior surface of the ice storage bin. The ice storage bin, operatively connected to the ozonated water generator, further includes an ozonated water outlet to provide ozonated water to the interior surface of the ice storage bin to sanitize the interior surface of the ice storage bin.

The ozonated water outlet may include a spray device. The ozonated water outlet may include multiple spray devices. The ozonated water outlet may include a drip system located near the plurality of sidewalls. The drip system may provide a continuous dripping of ozonated water to the interior surface of the ice storage bin. The spray device may sanitize the interior surface of the ice storage bin without removing ice therefrom. The drip system may sanitize the interior surface of the ice storage bin without removing ice therefrom.

A sanitizing system for ice storage equipment includes an ice storage bin and an ozonated water generator to create ozonated water. The ice storage bin includes a bottom, a plurality of sidewalls, and an ice receiving inlet. The plurality of sidewalls are disposed substantially perpendicular to the bottom of the ice storage bin to create an interior surface of the ice storage bin. The ice storage bin, operatively connected to the ozonated water generator, further includes an ozonated water outlet to provide ozonated water to the interior surface of the ice storage bin to sanitize the interior surface of the ice storage bin and descale the interior surface of the ice storage bin.

The ozonated water outlet may include a spray device. The ozonated water outlet may include multiple spray devices. The ozonated water outlet may include a drip system located near the plurality of sidewalls. The drip system may provide a continuous dripping of ozonated water to the interior surface of the ice storage bin.

The spray device may sanitize and descale the interior surface of the ice storage bin without removing ice therefrom. The drip system may sanitize and descale the interior surface of the ice storage bin without removing ice therefrom.

A method for sanitizing ice storage equipment includes (a) storing ice in an ice storage bin having sidewalls and a bottom surface; (b) generating ozonated water; and (c) dispersing the generated ozonated water on the sidewalls of the ice storage bin to sanitize an interior surface of the ice storage bin.

The ozonated water may be dispersed using a spray device. The ozonated water may be dispersed using multiple spray devices. The ozonated water may be dispersed using a drip system. The drip system may provide a continuous dripping of ozonated water to the interior surface of the ice storage bin. The spray device may sanitize the interior surface of the ice storage bin without removing ice therefrom.

A method for sanitizing ice storage equipment includes (a) storing ice in an ice storage bin having sidewalls and a bottom surface; (b) generating ozonated water; and (c) dispersing the generated ozonated water on the sidewalls of the ice storage bin to sanitize and descale an interior surface of the ice storage bin.

The ozonated water may be dispersed using a spray device. The ozonated water may be dispersed using multiple spray devices. The ozonated water may be dispersed using a drip system. The drip system may provide a continuous dripping of ozonated water to the interior surface of the ice storage bin. The spray device may sanitize and descale the interior surface of the ice storage bin without removing ice therefrom.

A sanitizing system for ice making equipment includes an ice producing subsystem and an ozonated water generation subsystem, operatively connected to the ice producing subsystem, to create ozonated water. The ice producing subsystem includes an evaporator, a water tray, a water distributor, and a pump. The ozonated water generation subsystem includes an ozonated water generator and ozonated water spraying devices. The ozonated water spraying devices is located within the ice producing subsystem. The ozonated water generation subsystem provides ozonated water to the ozonated water spraying devices so that the ozonated water spraying devices spray the water distributor with ozonated water.

The ozonated water spraying devices may spray the water tray with ozonated water. The ozonated water spraying devices may spray the evaporator with ozonated water.

A method for sanitizing ice making equipment includes (a) producing ice using an evaporator, a water tray, a water distributor, and a pump; (b) generating ozonated water; and (c) dispersing the generated ozonated water, using ozonated water spraying devices, on the water distributor to sanitize the water distributor.

The method may disperse the generated ozonated water, using ozonated water spraying devices, on the water distributor to sanitize the evaporator. The method may disperse the generated ozonated water, using ozonated water spraying devices, on the water distributor to sanitize the water tray.

An ozonated water generation system includes an ozonated water producing subsystem for producing ozonated water; an air purging device, operatively connected to the ozonated water producing subsystem, to purge ozone from the ozonated water generation system; a sensor, operatively connected to the ozonated water producing subsystem, to determine a concentration of ozone in the ozonated water; a controller for controlling operations of the ozonated water generation system; and a by-pass valve operatively connected to the sensor. The controller causes the by-pass valve to be opened when the sensor determines that the concentration of ozone in the ozonated water is below a predetermined level.

The ozonated water generation system may include a catalytic converter, operatively connected to the air purging device, to convert the ozone to oxygen. The sensor may be an oxidation-reduction potential sensor. The ozonated water producing subsystem may include multiple ozonated water generators detachably connected in series. Each ozonated water generator may include a replaceable ozone generator. The replaceable ozone generator may include a consumable U-shaped cathode and a titanium anode.

An ozone generator includes a consumable U-shaped cathode and a titanium anode.

An ozonated water generator includes a top portion and a bottom portion. The bottom portion is detachable from the top portion. The top portion includes a first coupler and a second coupler. The bottom portion includes an ozone generator. The ozone generator may include a consumable U-shaped cathode and a titanium anode.

An ozonated water dispensing device includes an ozonated water reservoir and a dispensing device. The dispensing device includes a processor, a pump, a sensor, a spraying device, and a transceiver. The processor disables the pump when the controller determines an amount of time that ozonated water in the ozonated water reservoir is beyond an effective life of the ozonated water.

The processor may determine, via the transceiver, an area being sprayed with the ozonated water.

It will be appreciated that variations of the above-disclosed embodiments and other features and functions, or alternatives thereof, may be desirably combined into many other different systems or applications. Also, various presently unforeseen or unanticipated alternatives, modifications, variations, or improvements therein may be subsequently made by those skilled in the art which are also intended to be encompassed by the description above and the following claims.

The invention claimed is:

1. A sanitizing system for ice storage equipment, comprising:
   an ice storage bin; and
   an ozonated water generator to create ozonated water;
   said ice storage bin including a bottom, a plurality of sidewalls, and an ice receiving inlet;
   said plurality of sidewalls being disposed substantially perpendicular to said bottom of said ice storage bin;
   said ice storage bin, operatively connected to said ozonated water generator, further including multiple ozonated water outlet devices located in said ice storage bin, each ozonated water outlet device being orientated to spray ozonated water only on said sidewalls and to minimize exposure of any ice in said ice storage bin to the sprayed ozonated water.

2. A sanitizing system for ice storage equipment, comprising:
   an ice storage bin;
   a de-mineralized water source; and
   an ozonated water generator to create ozonated water;
   said ice storage bin including a bottom, a plurality of sidewalls, and an ice receiving inlet;
   said plurality of sidewalls being disposed substantially perpendicular to said bottom of said ice storage bin to create an interior surface of said ice storage bin;
   said ice storage bin operatively connected to said de-mineralized water source and said ozonated water generator;
   said ice storage bin including multiple water outlet devices located in said ice storage bin, each water outlet device being orientated to spray de-mineralized water only on said sidewalls and to minimize exposure of any ice in said ice storage bin to the sprayed de-mineralized water;
   each water outlet device being orientated to spray ozonated water only on said sidewalls and to minimize exposure of any ice in said ice storage bin to the sprayed ozonated water.

* * * * *